United States Patent
You

(10) Patent No.: US 11,972,573 B2
(45) Date of Patent: Apr. 30, 2024

(54) METHOD OF AUTOMATICALLY RECOGNIZING WOUND BOUNDARY BASED ON ARTIFICIAL INTELLIGENCE AND METHOD OF GENERATING THREE-DIMENSIONAL WOUND MODEL

(71) Applicant: ROKIT HEALTHCARE INC., Seoul (KR)

(72) Inventor: Seok Hwan You, Seoul (KR)

(73) Assignee: ROKIT HEALTHCARE INC., Seoul (KR)

( * ) Notice: Subject to any disclaimer, the term of this patent is extended or adjusted under 35 U.S.C. 154(b) by 391 days.

(21) Appl. No.: 17/441,955

(22) PCT Filed: Jun. 10, 2021

(86) PCT No.: PCT/KR2021/007257
§ 371 (c)(1),
(2) Date: Sep. 22, 2021

(87) PCT Pub. No.: WO2022/131461
PCT Pub. Date: Jun. 23, 2022

(65) Prior Publication Data
US 2022/0398739 A1 Dec. 15, 2022

(30) Foreign Application Priority Data

Dec. 14, 2020 (KR) ........................ 10-2020-0174232

(51) Int. Cl.
*G06T 7/13* (2017.01)
*A61B 5/00* (2006.01)
(Continued)

(52) U.S. Cl.
CPC ................ *G06T 7/13* (2017.01); *A61B 5/445* (2013.01); *G06T 7/0012* (2013.01); *G06T 17/00* (2013.01);
(Continued)

(58) Field of Classification Search
None
See application file for complete search history.

(56) References Cited

U.S. PATENT DOCUMENTS

2008/0317308 A1* 12/2008 Wu ........................ G06T 7/0012
382/128
2012/0035469 A1 2/2012 Whelan et al.
(Continued)

FOREIGN PATENT DOCUMENTS

CN 106663411 A * 5/2017 ............. G02B 27/01
CN 110310285 B * 12/2022 ............. G06T 17/00
(Continued)

OTHER PUBLICATIONS

Juszczyk, Jan Maria et al. "Wound 3D Geometrical Feature Estimation Using Poisson Reconstruction" IEEE Access, Oct. 30, 2020, 9, 7894-7907 (14 pages).
(Continued)

*Primary Examiner* — Mohammed Rachedine
(74) *Attorney, Agent, or Firm* — Osha Bergman Watanabe & Burton LLP

(57) ABSTRACT

The present specification discloses a method capable of automatically recognizing an accurate wound boundary and a method of generating a 3D wound model based on the recognized wound boundary. The method of automatically recognizing a wound boundary according to the present specification is a method of automatically recognizing a wound boundary based on artificial intelligence, and may photograph several frames of the wound to be recognized with an RGB-D camera, separating measurement information in an image, amplifying image data for learning, and passing the amplified image data through an artificial neural network. The method may include generating a three-dimensional (3D) model by performing boundary recognition (Continued)

post-processing on the data passing through the artificial neural network to match a two-dimensional (2D) image with the 3D model.

10 Claims, 22 Drawing Sheets

(51) Int. Cl.
| | |
|---|---|
| *A61B 5/02* | (2006.01) |
| *A61B 34/10* | (2016.01) |
| *A61F 2/10* | (2006.01) |
| *A61L 27/60* | (2006.01) |
| *B33Y 40/00* | (2020.01) |
| *B33Y 70/00* | (2020.01) |
| *G06N 3/09* | (2023.01) |
| *G06N 3/092* | (2023.01) |
| *G06T 7/00* | (2017.01) |
| *G06T 17/00* | (2006.01) |
| *G16H 50/20* | (2018.01) |

(52) U.S. Cl.
CPC ......... *A61B 5/0064* (2013.01); *A61B 2576/00* (2013.01); *G06T 2200/04* (2013.01); *G06T 2207/10028* (2013.01); *G06T 2207/30088* (2013.01)

(56) References Cited

U.S. PATENT DOCUMENTS

| | | |
|---|---|---|
| 2018/0021140 A1 | 1/2018 | Angelini et al. |
| 2018/0182121 A1* | 6/2018 | Xu .............................. G06T 7/13 |
| 2021/0290152 A1* | 9/2021 | Vogel ..................... G16H 40/67 |

FOREIGN PATENT DOCUMENTS

| | | | |
|---|---|---|---|
| KR | 2016-0092424 A | 8/2016 | |
| KR | 2019-0101758 A | 9/2019 | |
| WO | WO-2016130953 A1 * | 8/2016 | ......... A61F 2/30942 |

OTHER PUBLICATIONS

International Search Report issued in International Application No. PCT/KR2021/007257 dated Sep. 24, 2021 (3 pages).

\* cited by examiner

[Fig. 1]
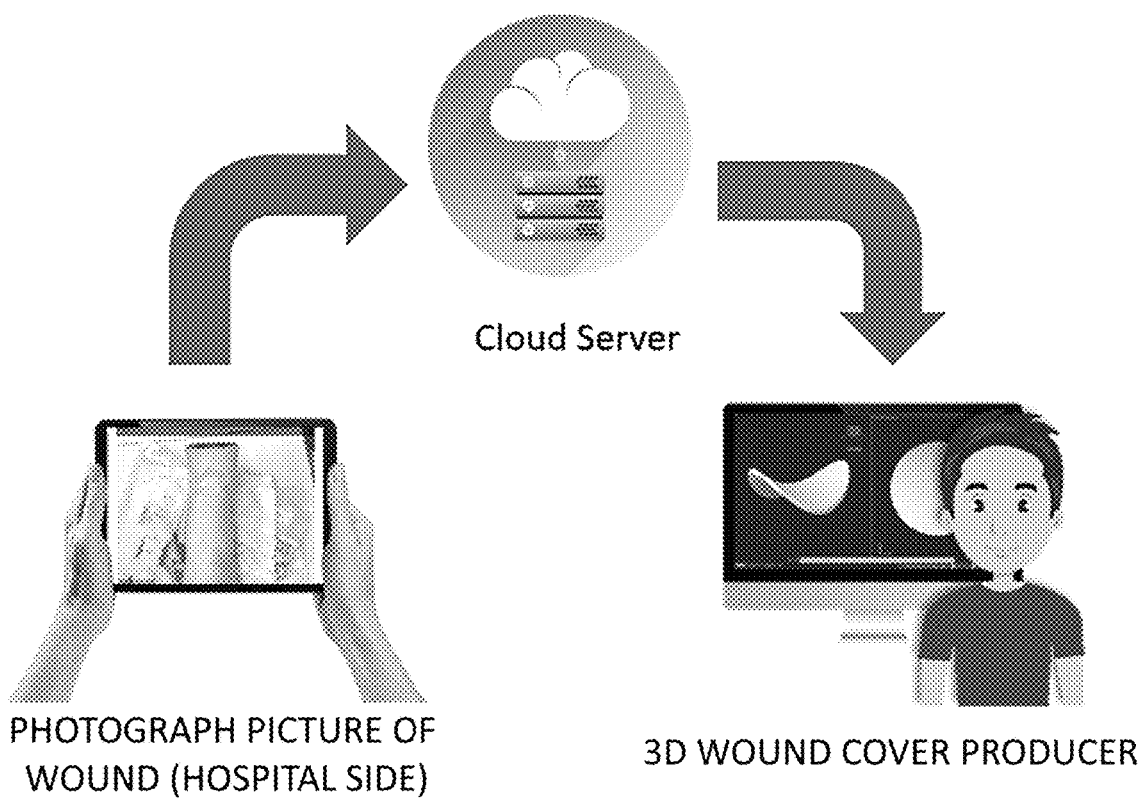

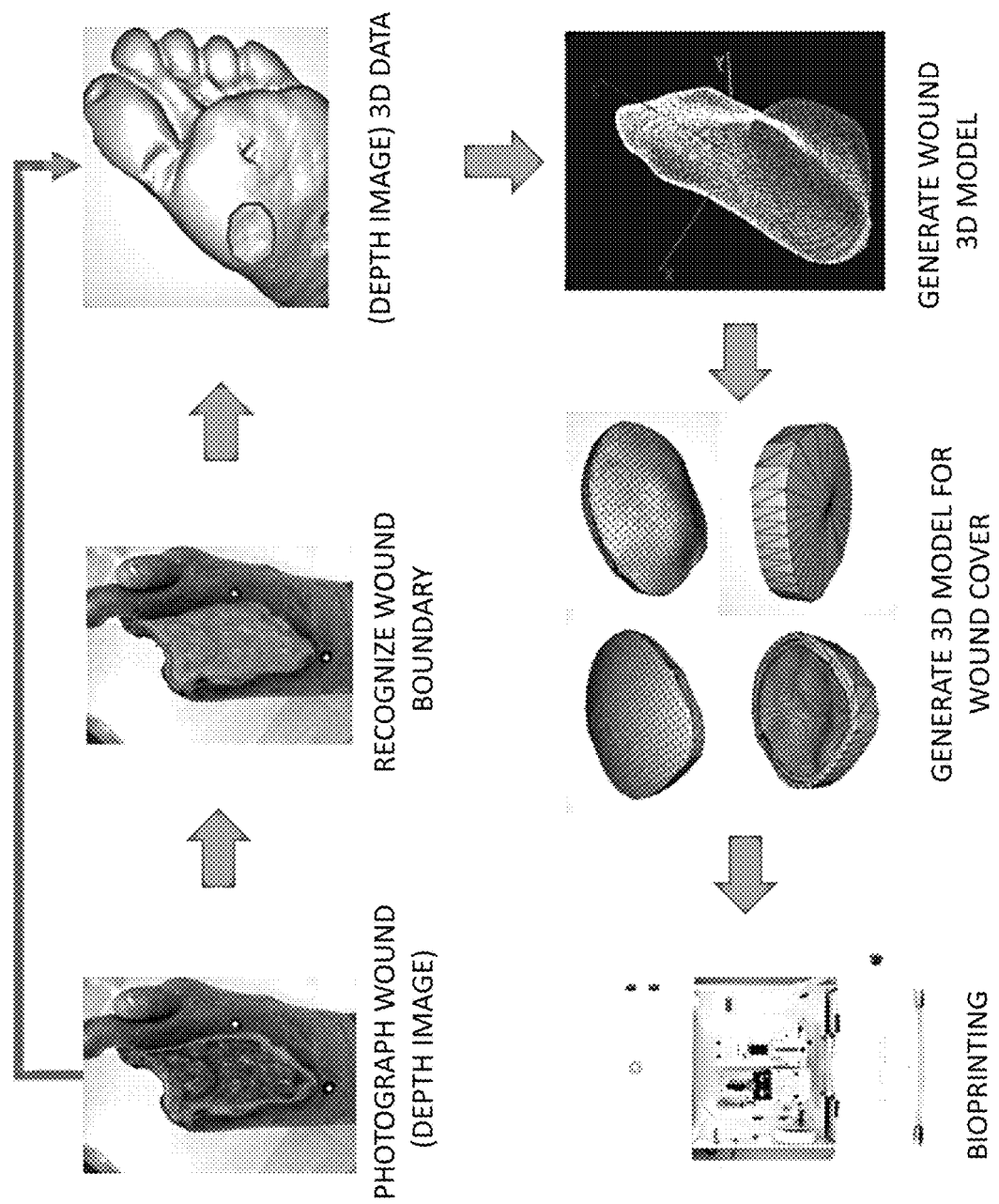
[Fig. 2]

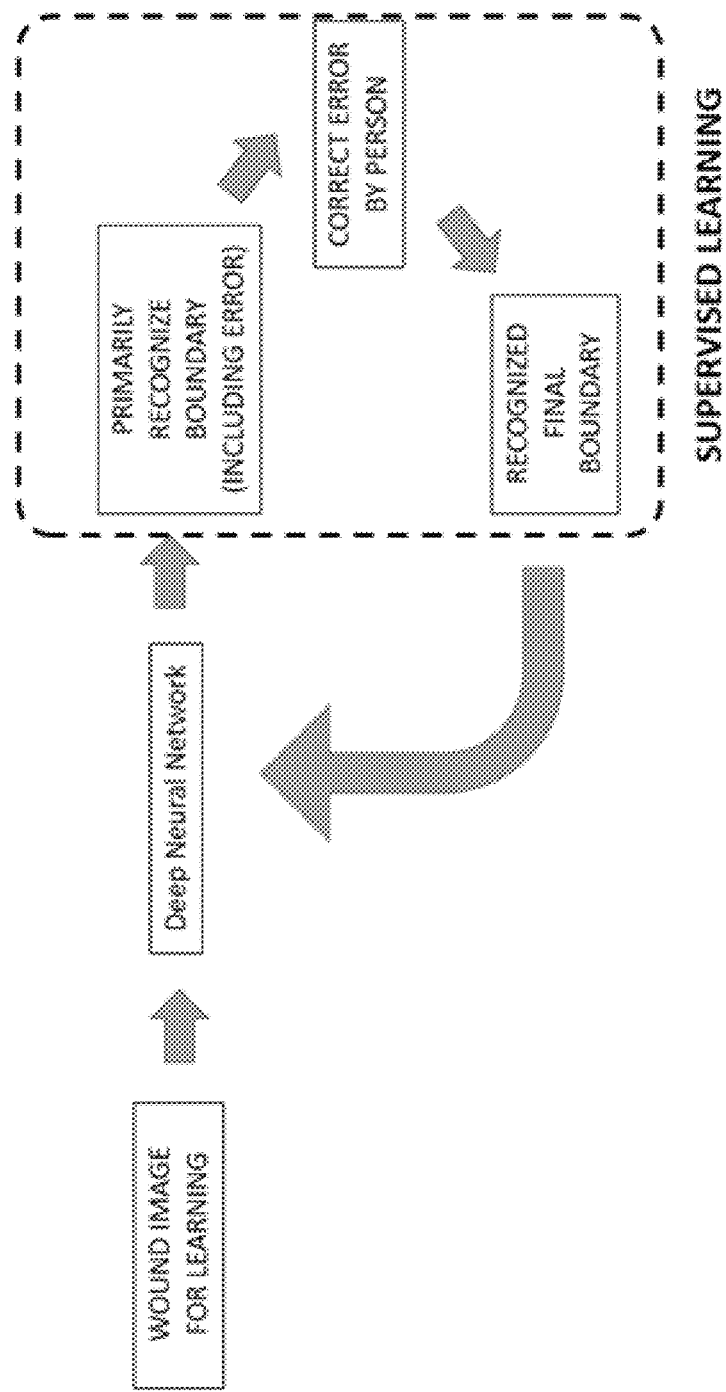
[Fig. 3]

[Fig. 4]
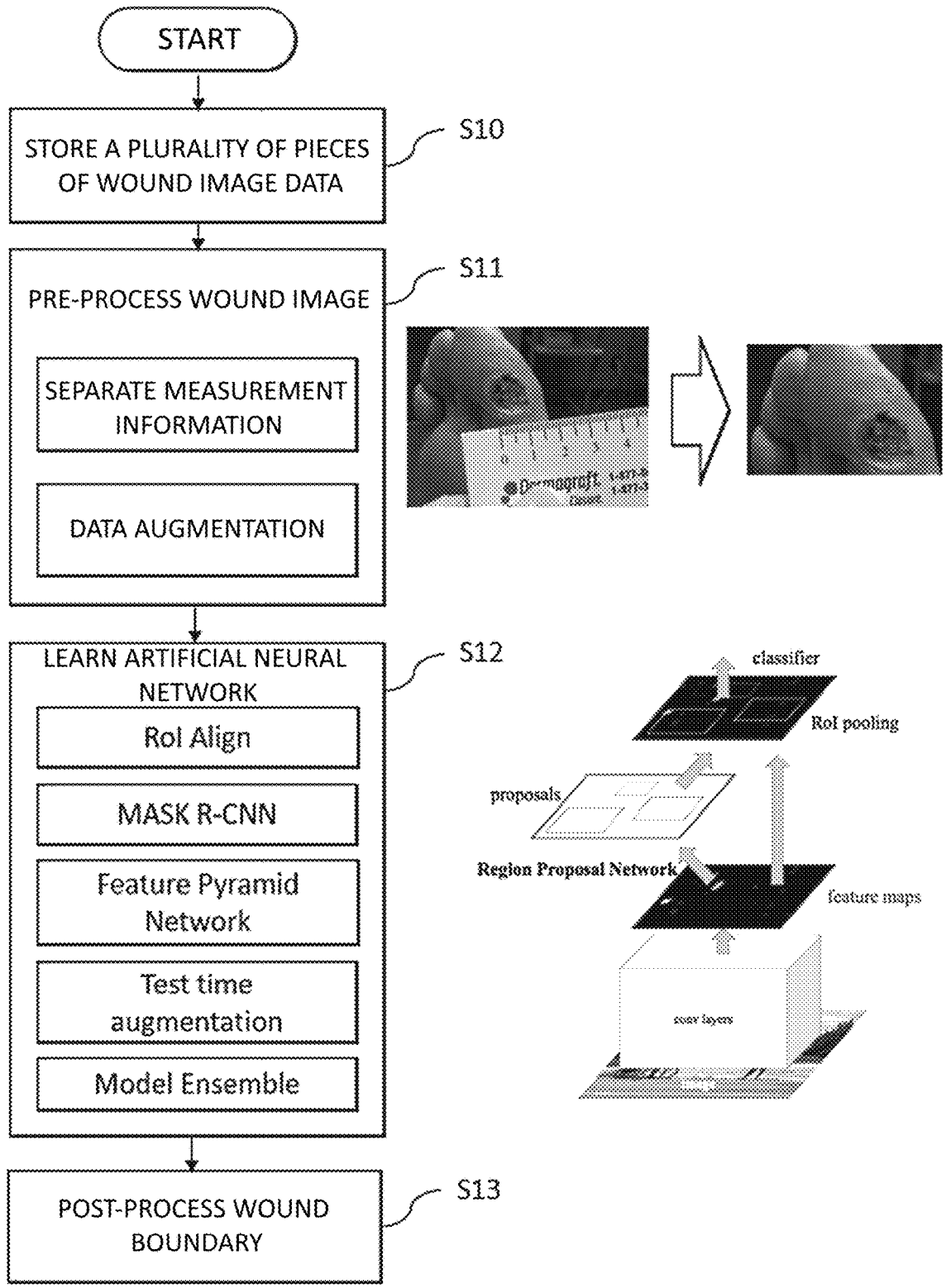

[Fig. 5A]
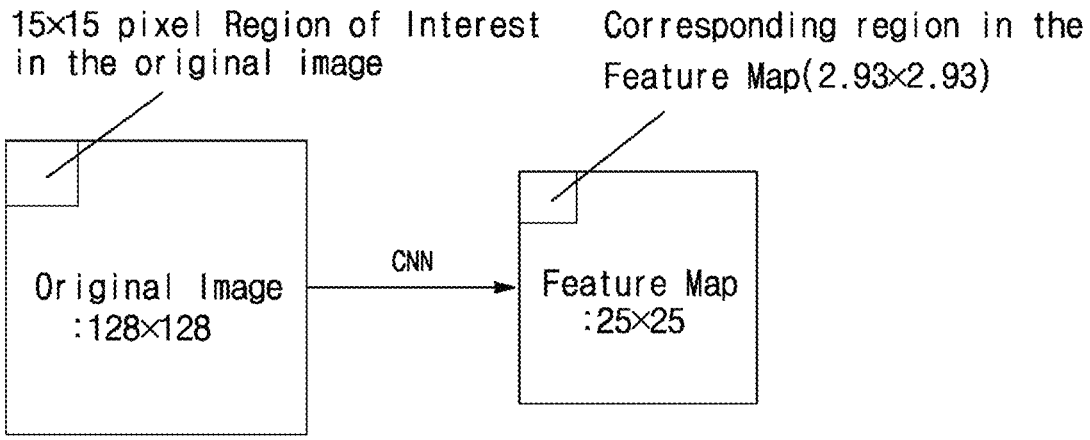
[Fig. 5B]
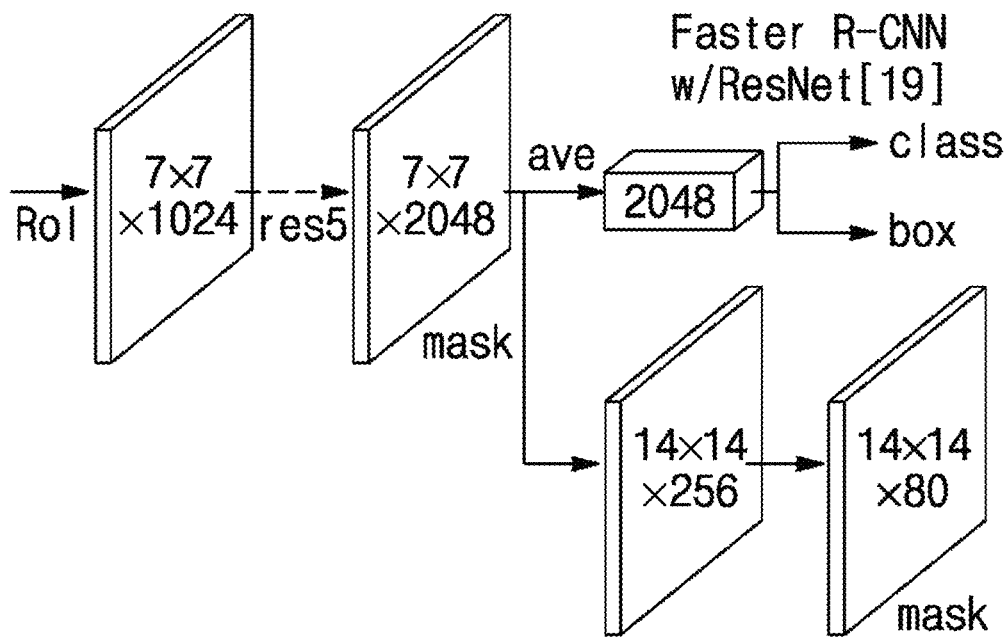
[Fig. 5C]
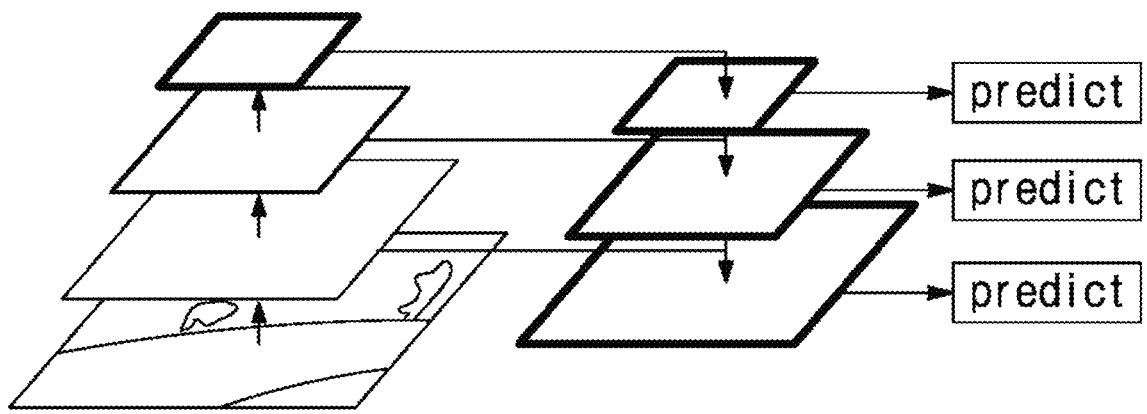

[Fig. 5D]
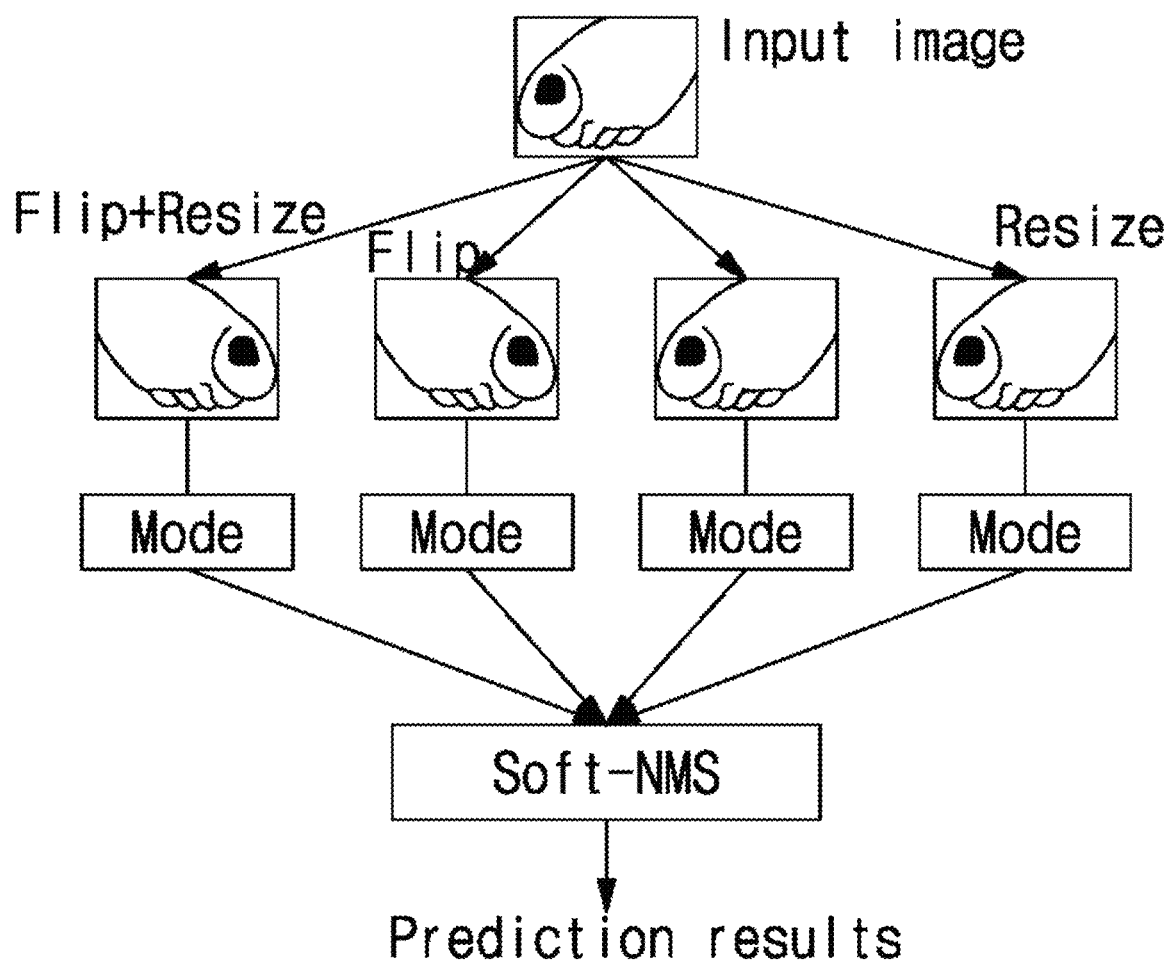

[Fig. 5E]
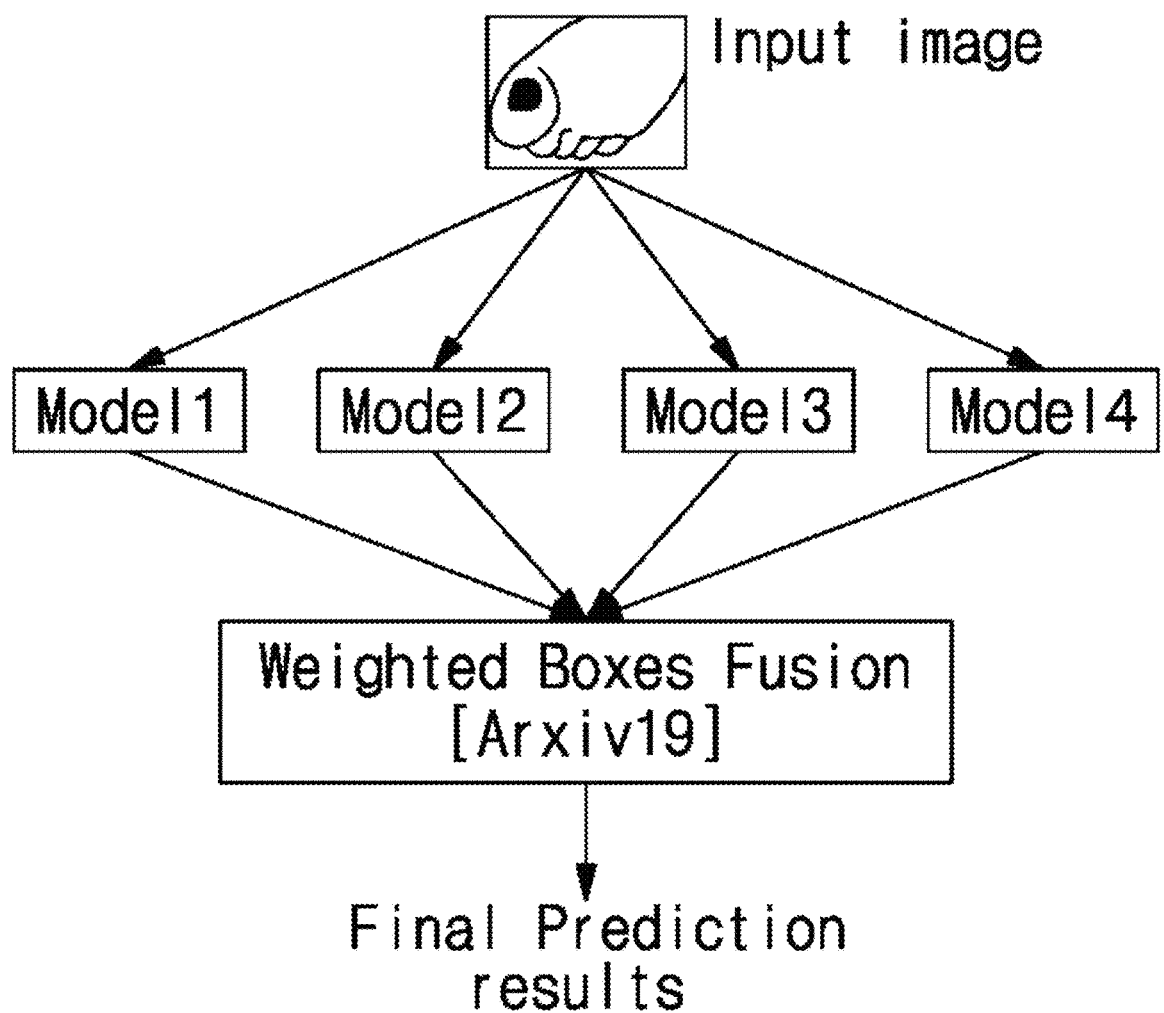

[Fig. 6]
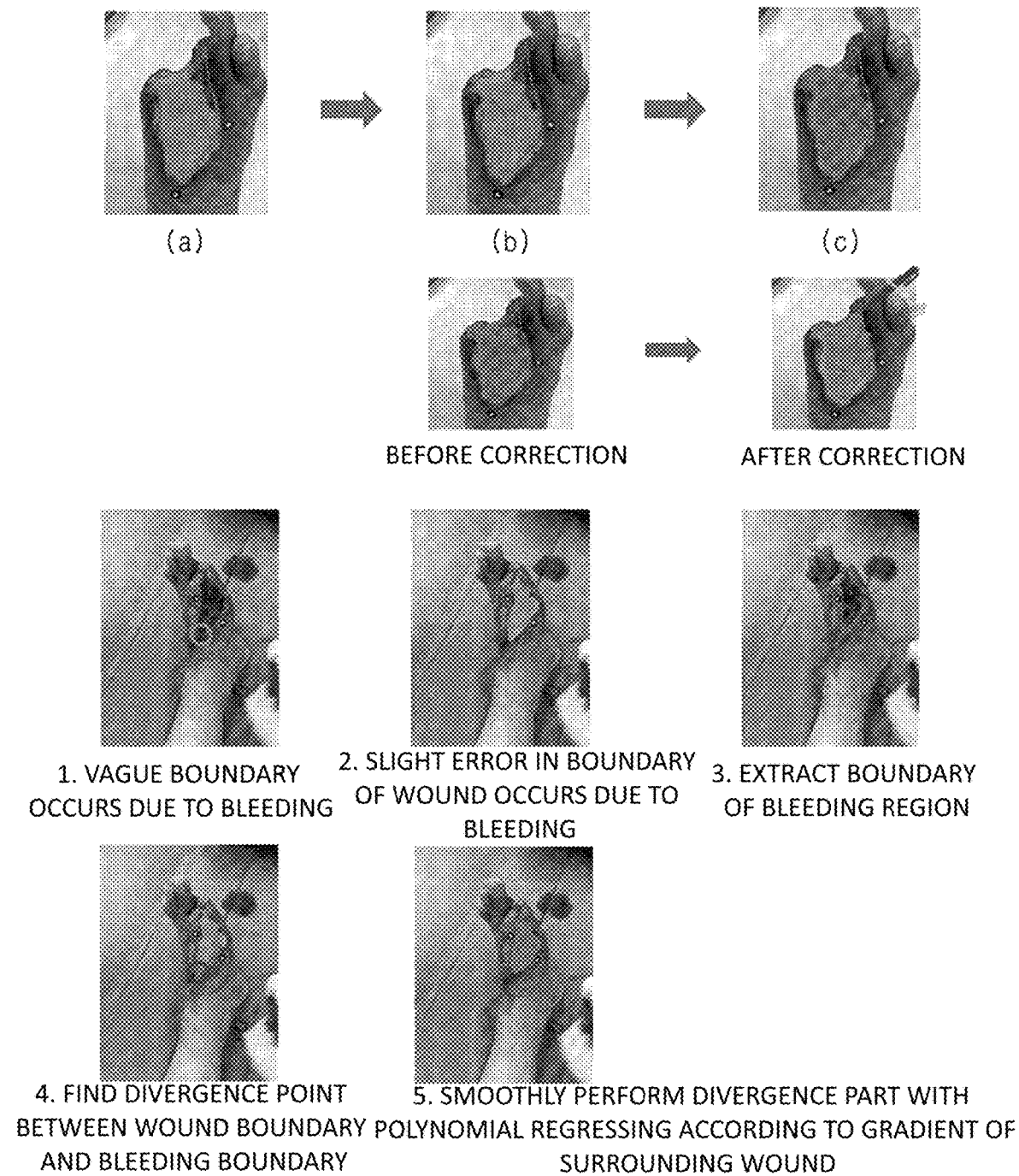

[Fig. 7]
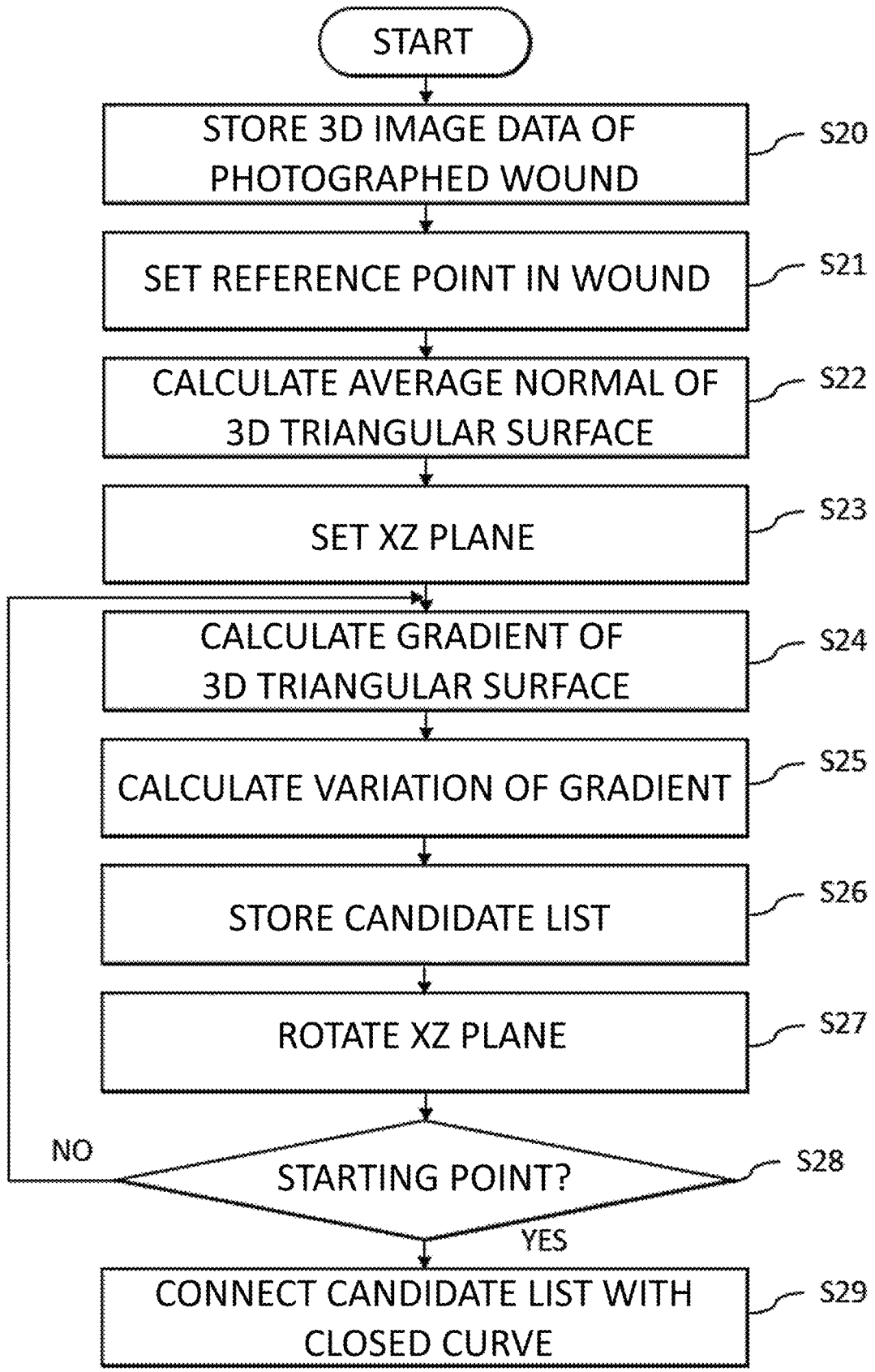

[Fig. 8A]
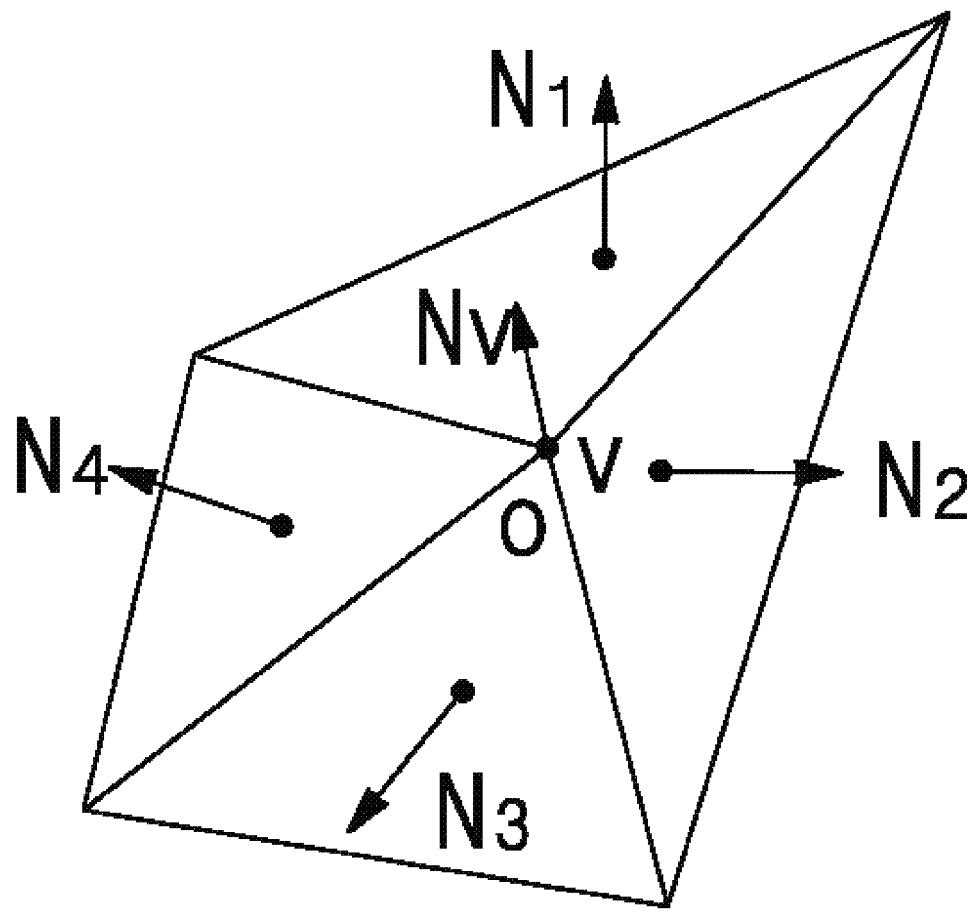

[Fig. 8B]
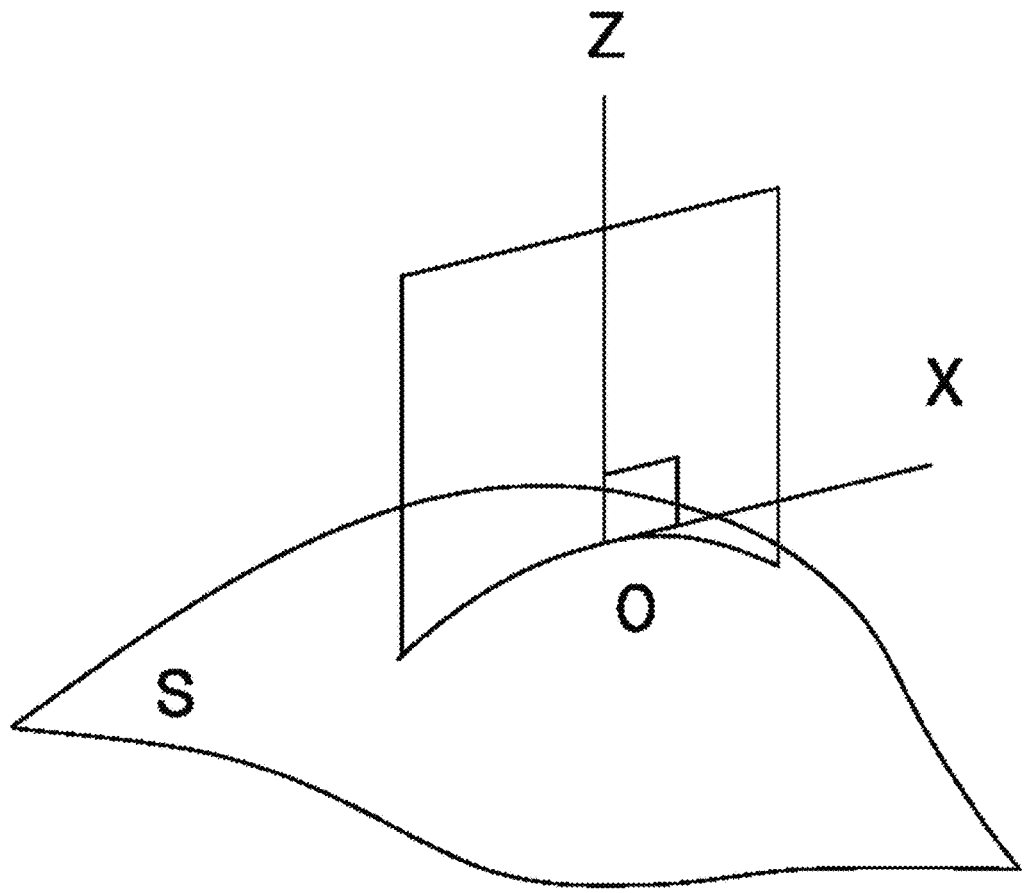
[Fig. 8C]
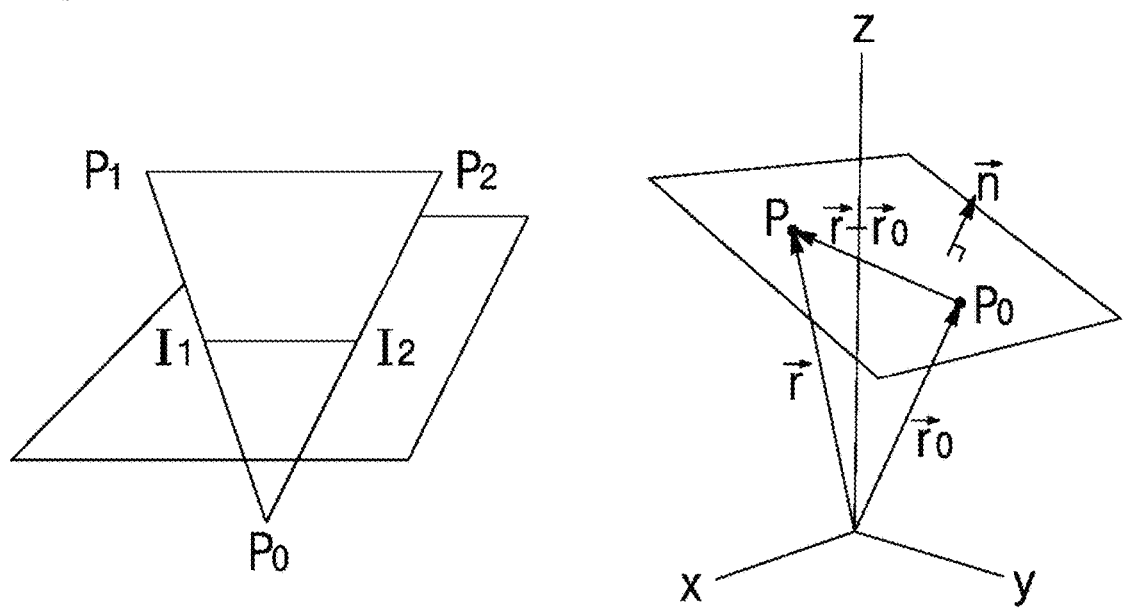

[Fig. 9A]
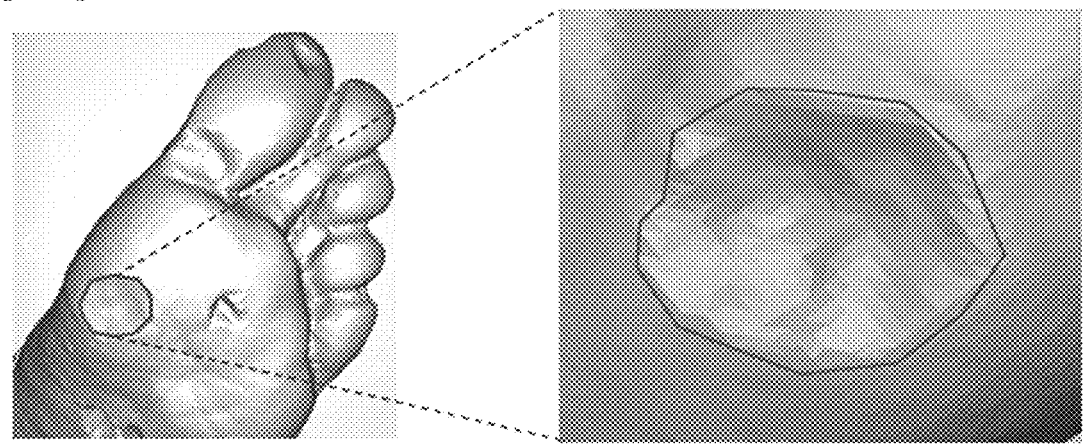
[Fig. 9B]
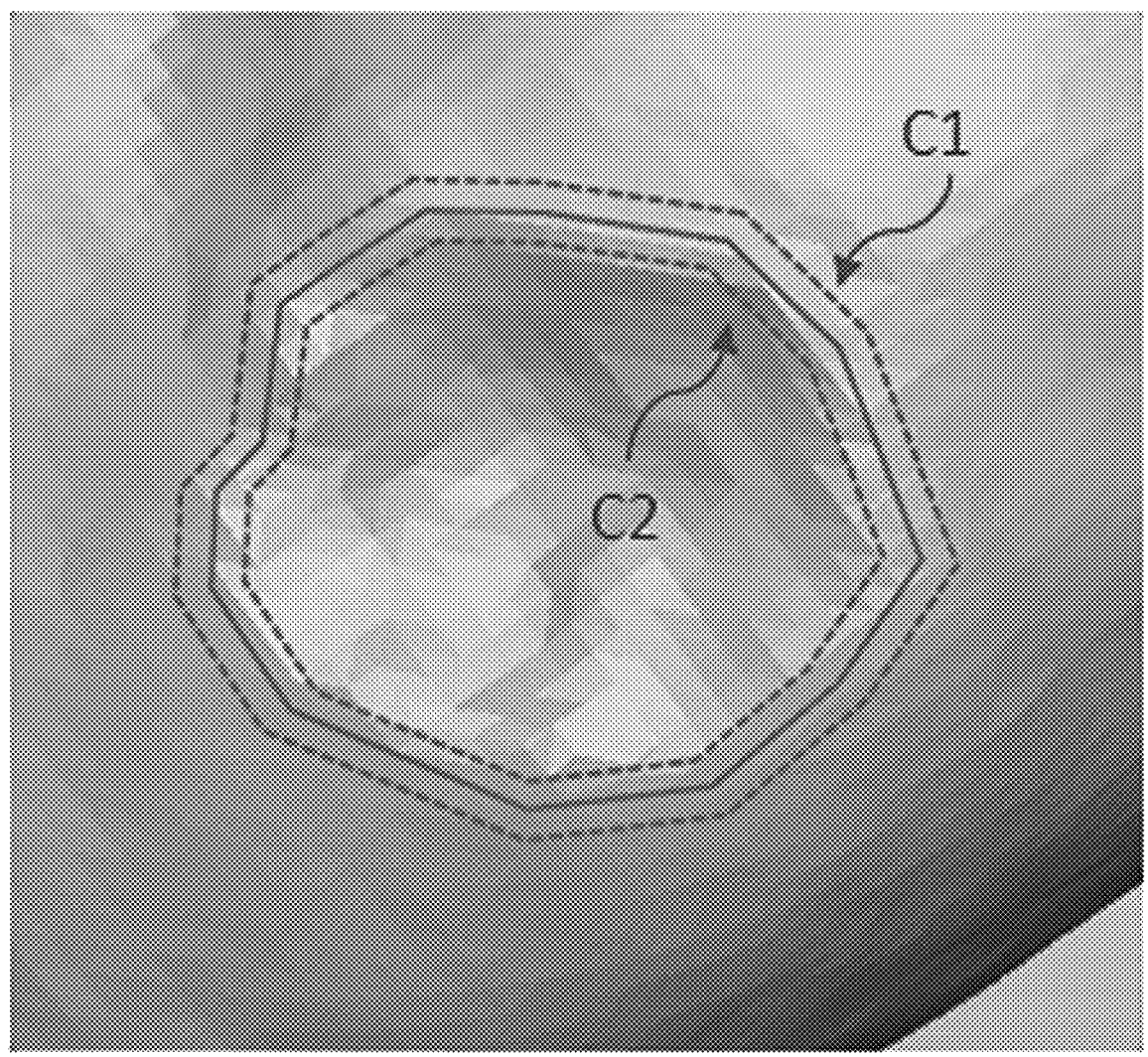

[Fig. 9C]
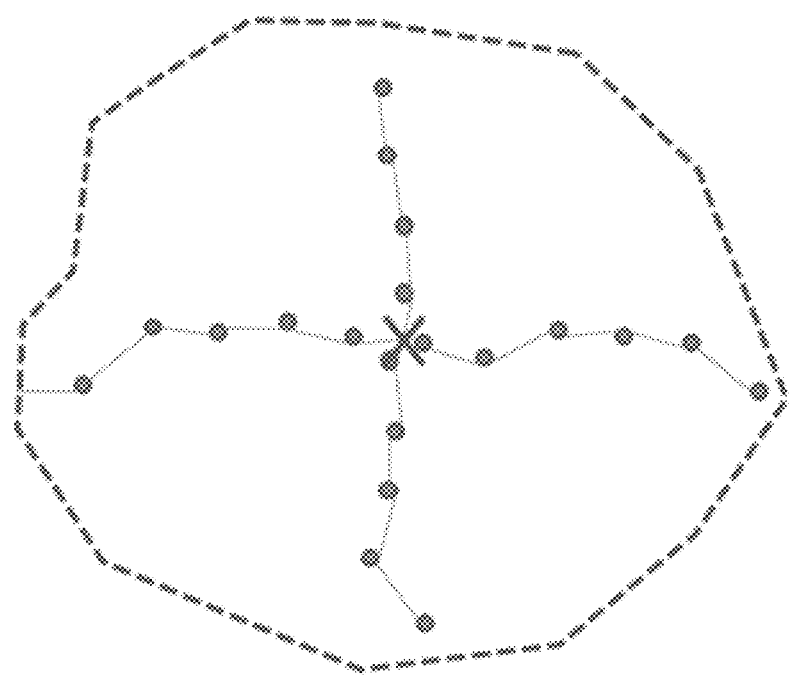

[Fig. 9D]
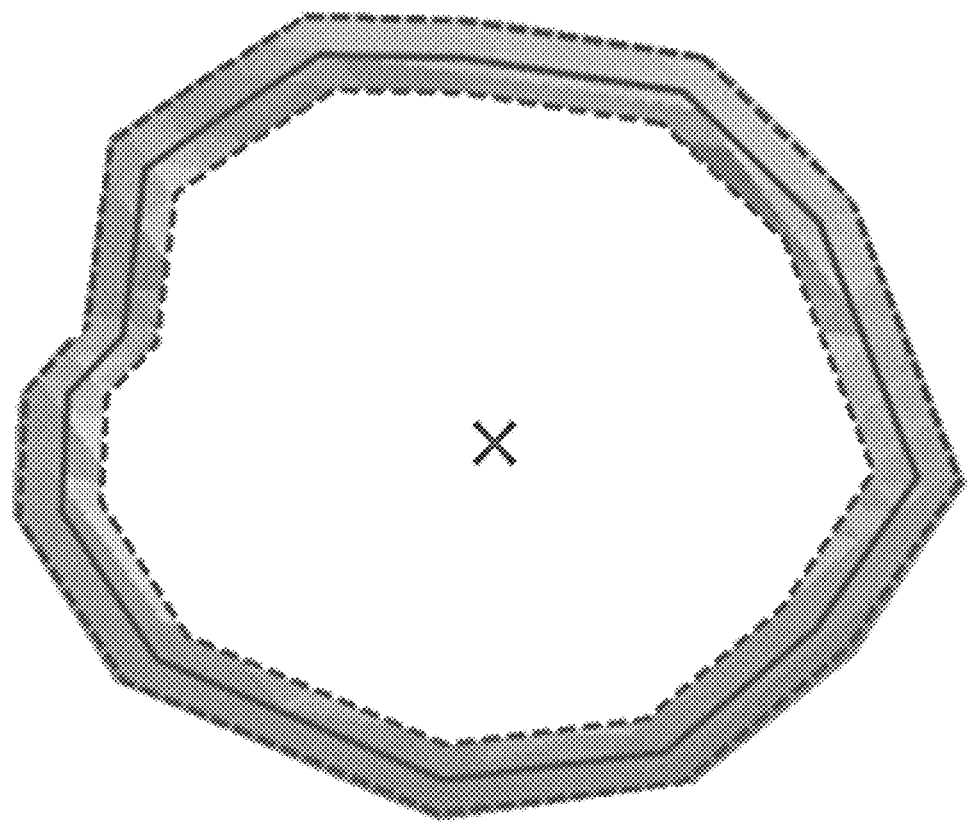

[Fig. 10]
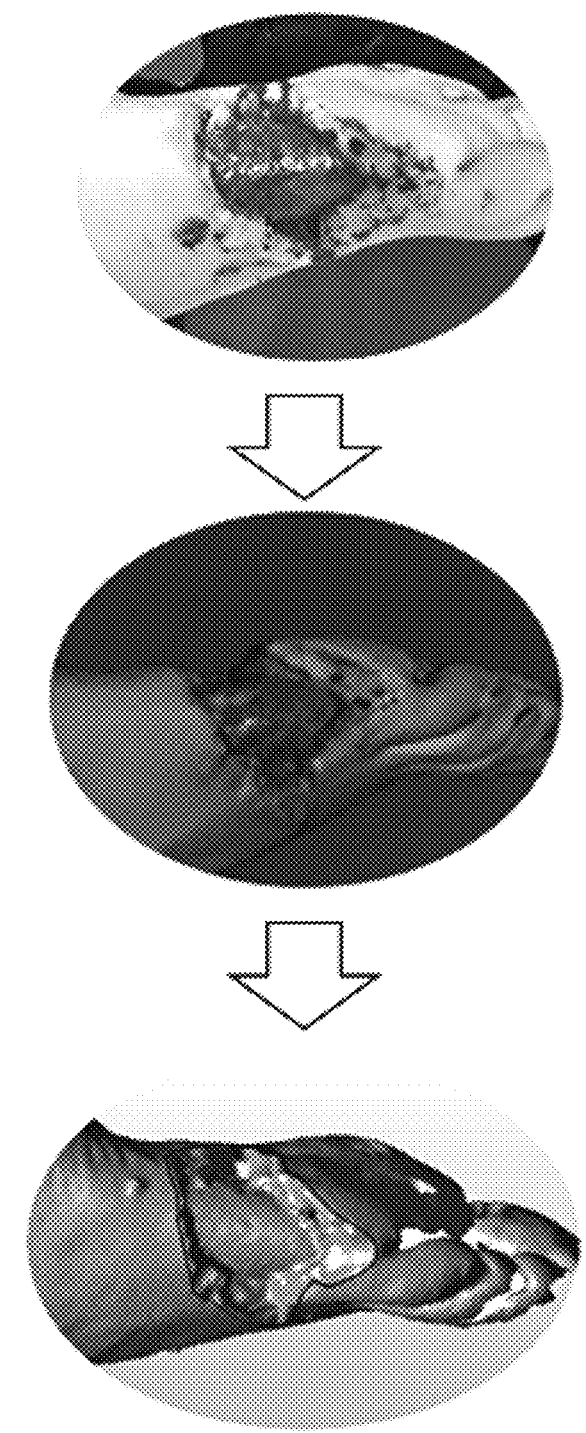

[Fig. 11]
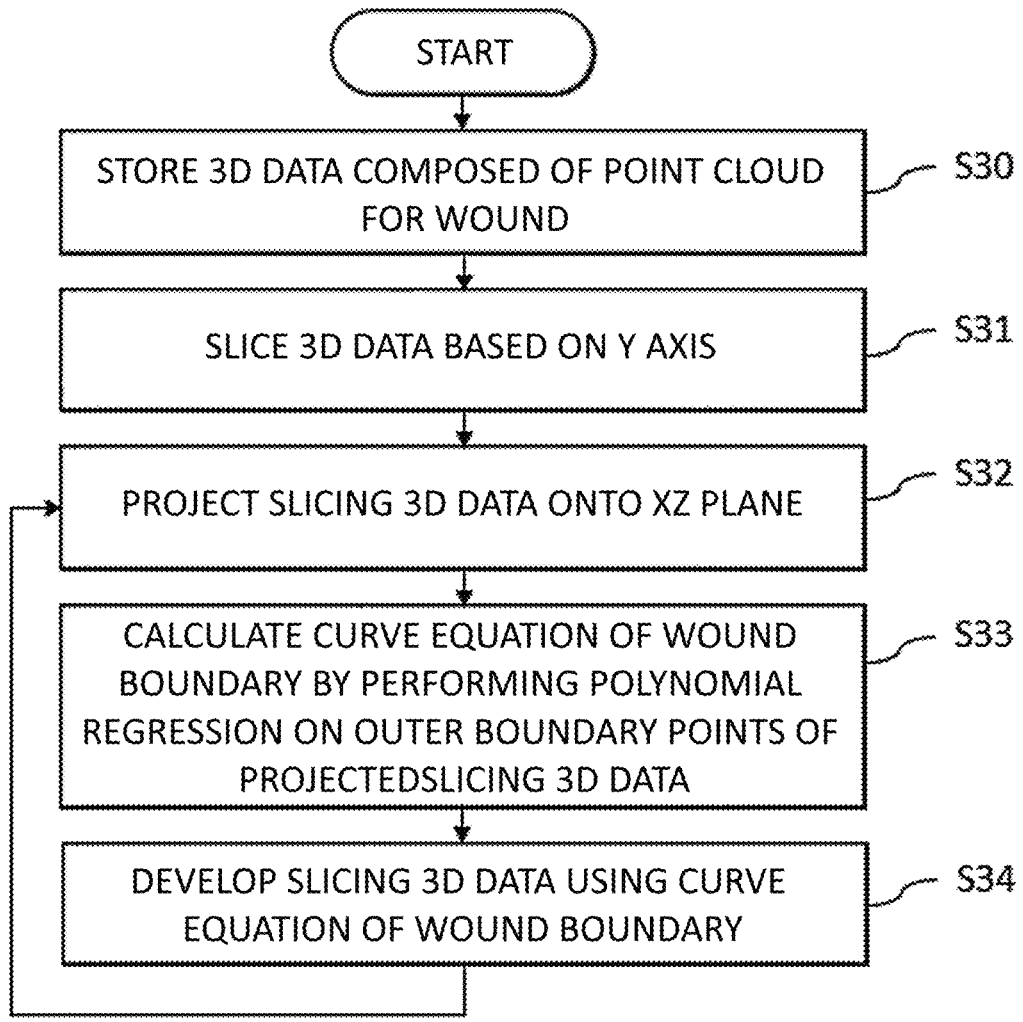
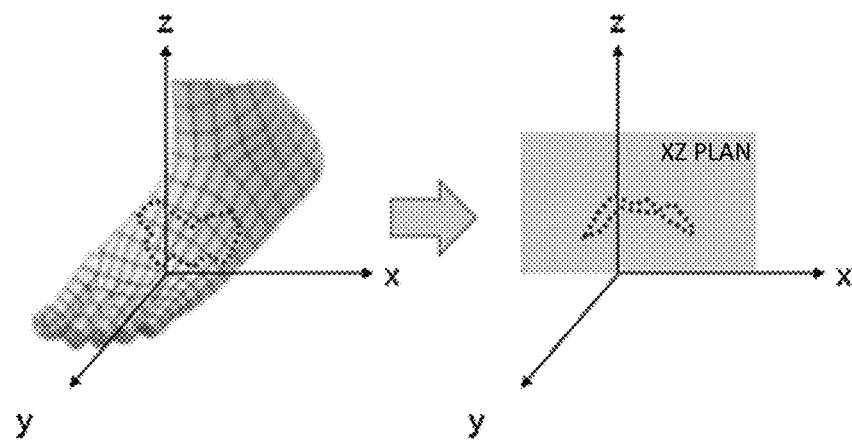

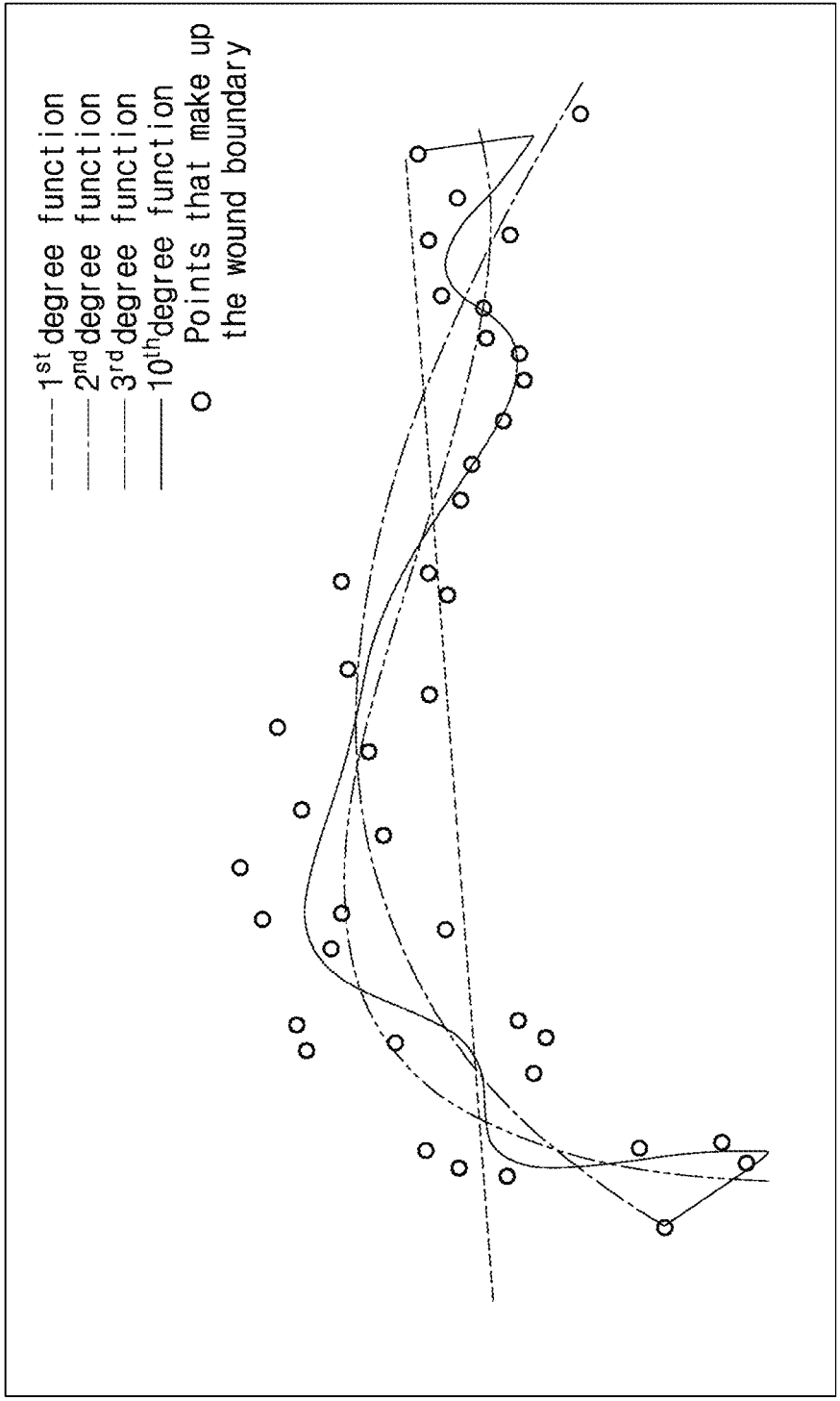
[Fig. 12]

[Fig. 13]
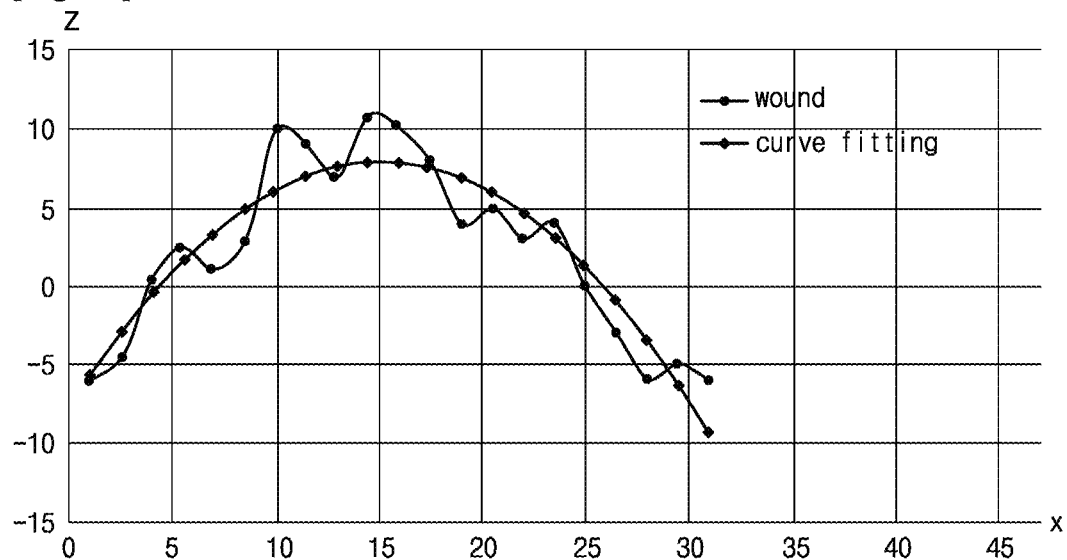
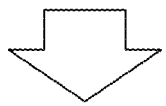
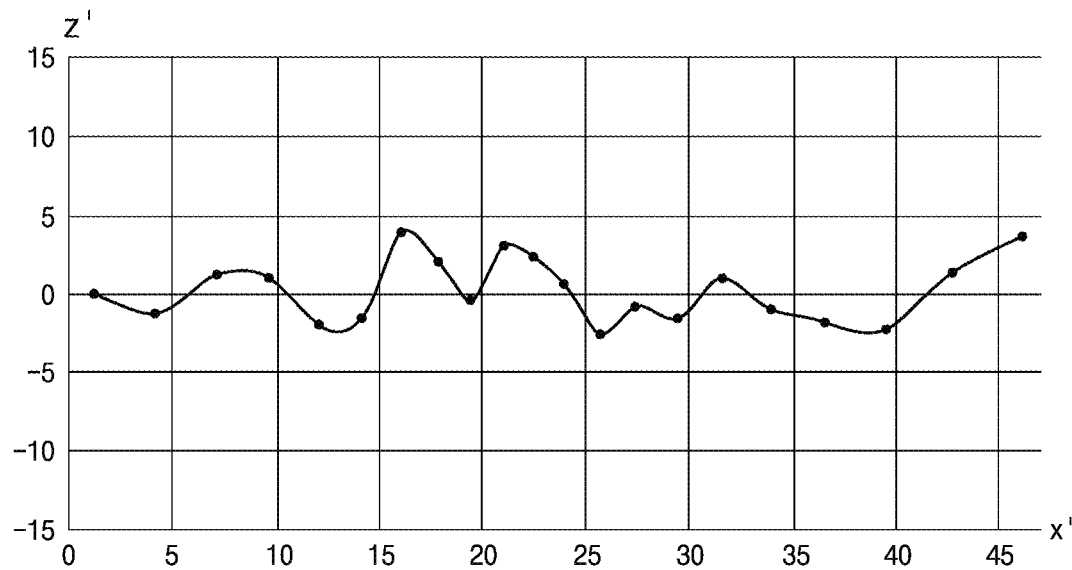

[Fig. 14]
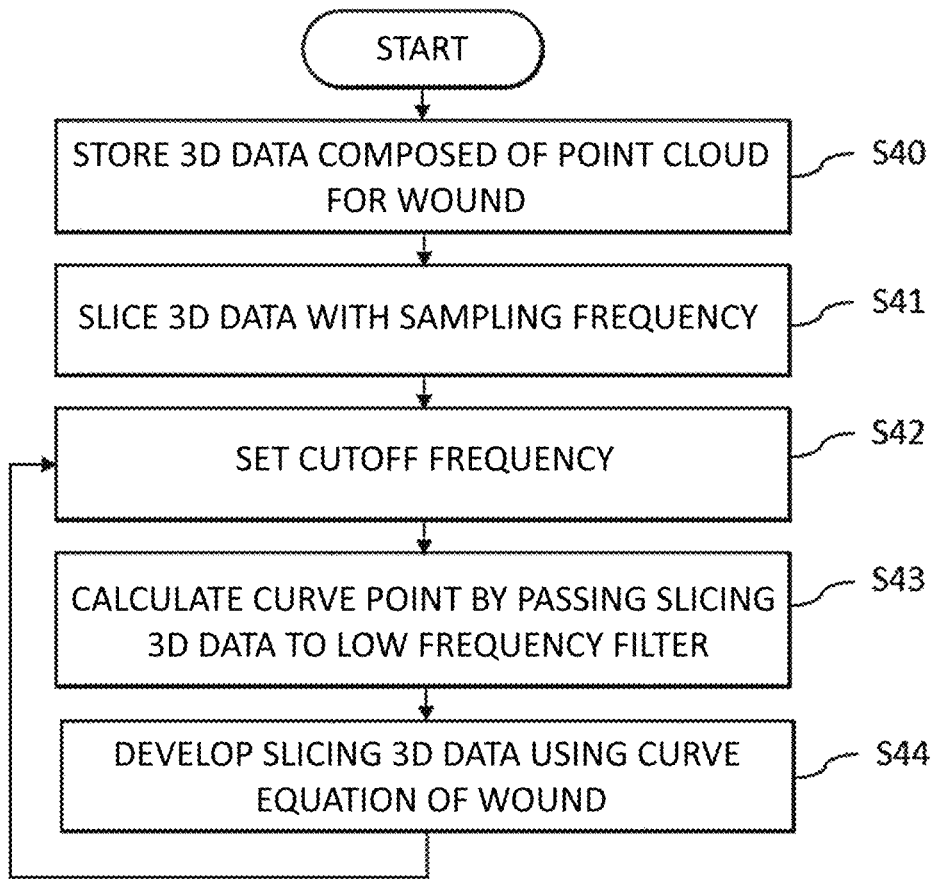
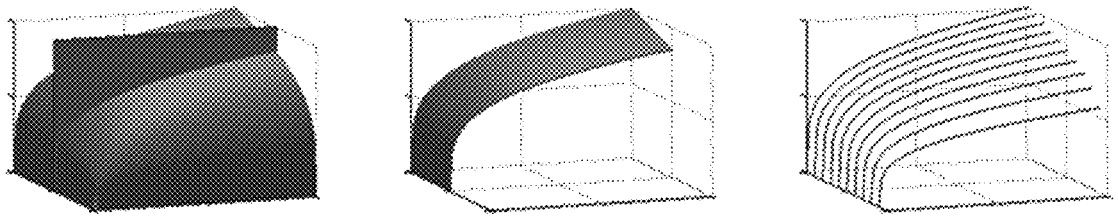

[Fig. 15]
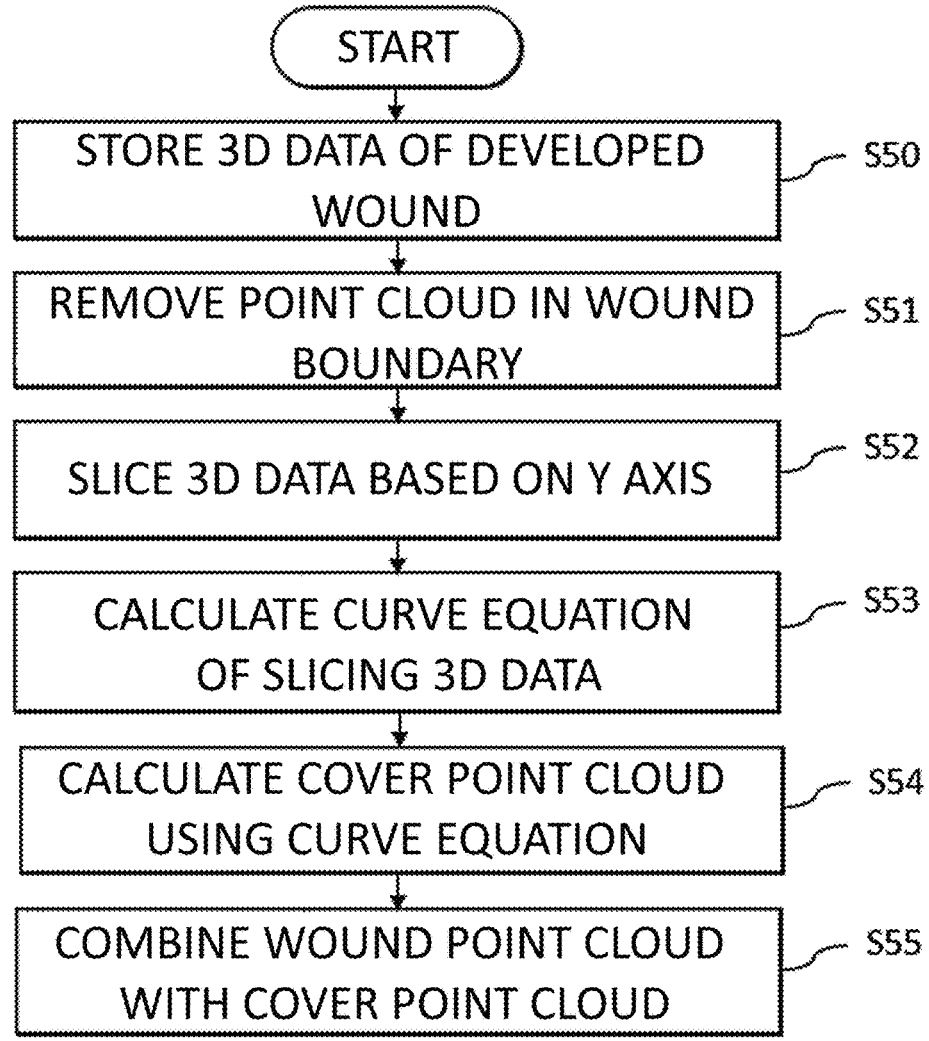
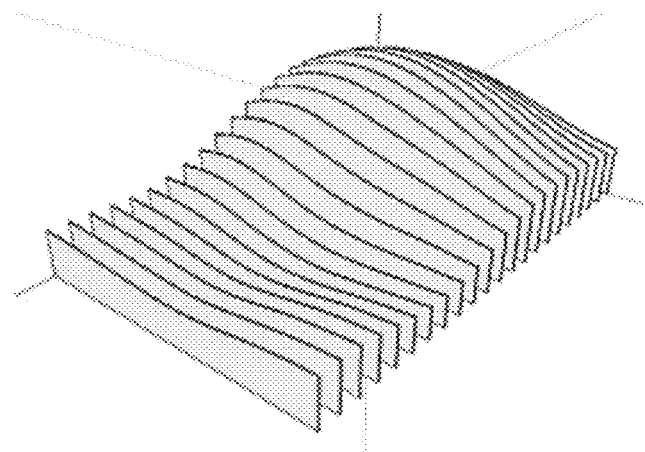

[Fig. 16]
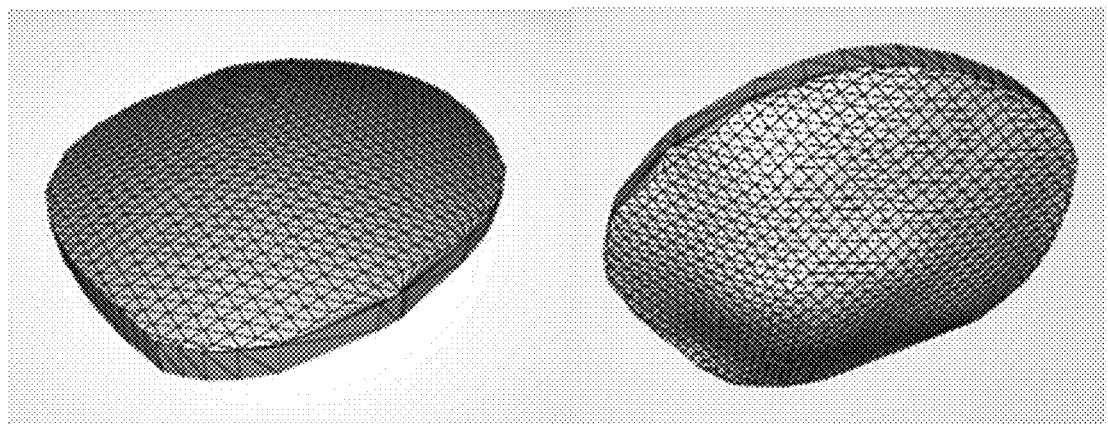
UPPER PORTION    LOWER PORTION

[Fig. 17]
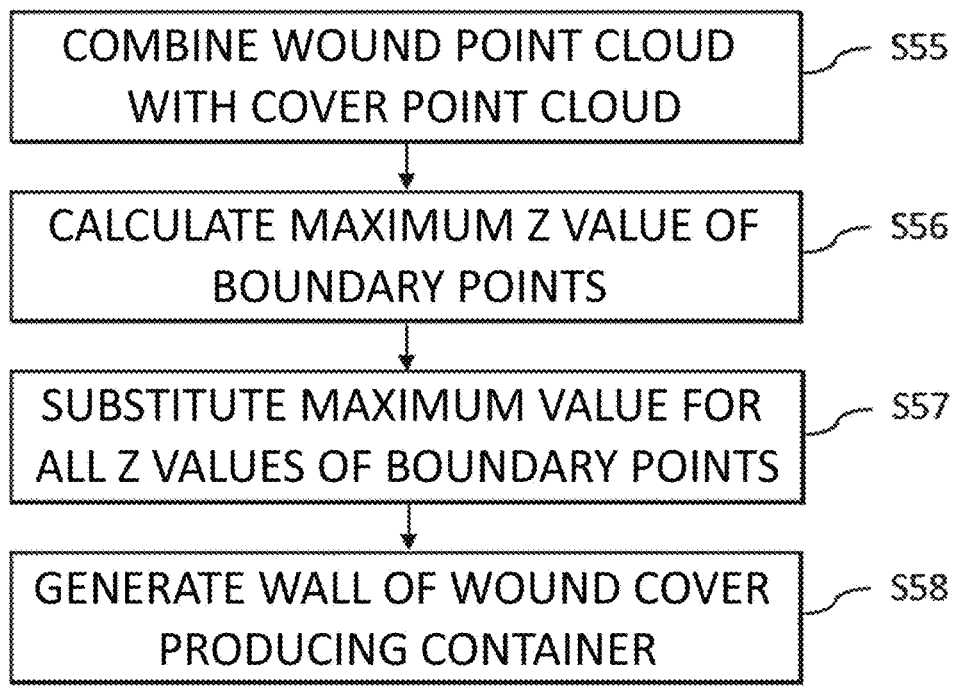
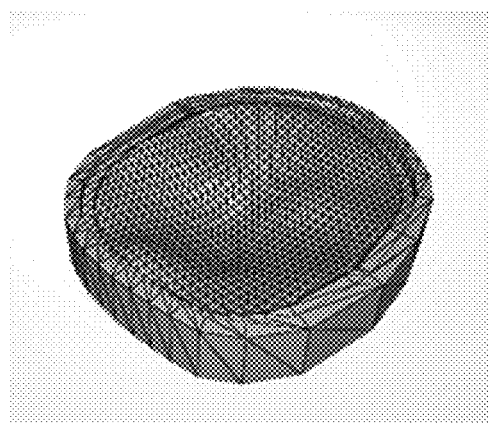
UPPER PORTION
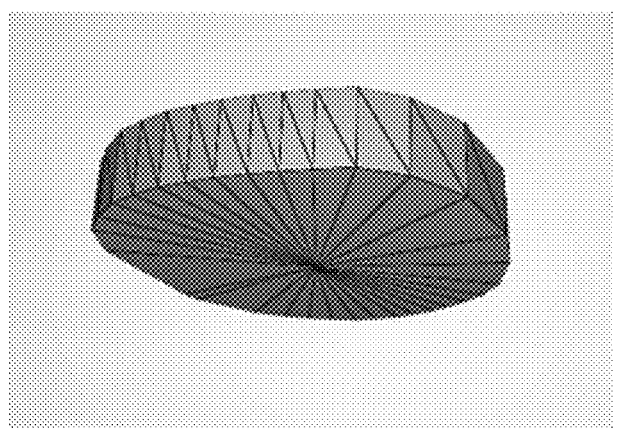
LOWER PORTION

METHOD OF AUTOMATICALLY RECOGNIZING WOUND BOUNDARY BASED ON ARTIFICIAL INTELLIGENCE AND METHOD OF GENERATING THREE-DIMENSIONAL WOUND MODEL

TECHNICAL FIELD

The present disclosure relates to three-dimensional (3D) image processing using artificial intelligence, and more particularly, to a technology for automatically recognizing a wound boundary using artificial intelligence in a 3D image of the photographed wound.

BACKGROUND ART

This application claims priority to Korean Patent Application No. 10-2020-0174232, filed on Dec. 14, 2020, and all contents disclosed in specification and drawings of the application are incorporated herein by reference.

The content described in this section merely provides background information for embodiments disclosed in the present specification, and does not constitute the related art.

Three-dimensional (3D) bioprinting, which is a field of application and development of a 3D printing technology, is based on the 3D printing technology, and is a technology for creating a desired shape by combining an extracellular matrix (hereinafter, referred to as ECM) such as collagen or bio-ink imitating the extracellular matrix with cells and other biomaterials. Currently, various methods for the 3D bioprinting are being developed according to the desired purpose and biological environment, and various bio-inks are also being studied.

Such 3D bioprinting constructs the ECM or the bio-ink into a desired shape, and by culturing cells necessary for the ECM or the bio-ink, living organs or tissues having the same functions as they do in reality are produced. One of the most important issues in the 3D bioprinting is to enable cells and biomaterials as materials to be stored and used as stably as possible so that the cells may continue to function without dying.

One of the important factors influencing the quality of outputs in 3D bioprinting is how well the outputs match wounds. To this end, a process of accurately photographing the 3D shapes of the wounds and 3D modeling the photographed 3D shapes needs to be handled as an important process.

DISCLOSURE

Technical Problem

An object of the present specification is to provide a method of automatically recognizing an accurate wound boundary and a method of generating a three-dimensional (3D) wound model based on the recognized wound boundary.

The present disclosure is not limited to the above-mentioned objects, and other objects that are not mentioned may be obviously understood by those skilled in the art from the following description.

Technical Solution

A method of recognizing a wound boundary using three-dimensional (3D) image data of the photographed wound includes: (a) storing, by processor, the 3D image data of the photographed wound; (b) setting, by processor, a point located inside the wound in the image data as a reference point; (c) calculating, by processor, an average normal of triangles (hereinafter, "3D triangular surfaces") formed by point clouds included in a preset radius around the reference point, and setting, by processor, a plane including the average normal and a first axis perpendicular to the normal; (d) calculating, by processor, intersection points between the plane and each of the 3D triangular surfaces, and calculating, by processor, gradients of each of the 3D triangular surfaces using the intersection point; (e) calculating, by processor, variations of gradients of adjacent 3D triangular surfaces in a direction away from the reference point; (f) storing, by processor, as a candidate list, a starting point having a length that is maintained at greater than or equal to a reference length value in which a length connecting the 3D triangular surfaces connected to each other among the 3D triangular surfaces related to the variations of the gradients is maintained at a preset reference gradient change value or less among the calculated variations of the gradients; (g) accumulating, by processor, the candidate list stored in the operation (f) while rotating the plane set in the operation (c) at a preset angle using the average normal as a rotation axis and repeating the operations (d) to (f); and (h) forming, by processor, a closed curve by connecting adjacent starting points within a preset reference distance among the starting points included in the accumulated candidate list.

The operation (b) may include setting coordinates input by a user as the reference point.

The normal may be a Z axis, the first axis may be an X axis, and the plane may be an XZ plane.

The operation (g) may include rotating the plane clockwise by 0.1°.

The operation (h) may include, when a plurality of closed curves are formed, selecting a closed curve including the reference point therein from among the plurality of closed curves.

The operation (h) may further include, when there are the plurality of closed curves including the reference point therein, selecting a largest closed curve.

The operation (a) may include: (a-1) receiving, by processor, temporary boundary line data including the 3Dd image data of the photographed wound and a boundary of the wound; and (a-2) generating, by processor, a first closed curve extending by a preset length based on the temporary boundary line and a second closed curve reduced by the preset length.

The operation (b) may include setting, as the reference point, an intersection point where two imaginary lines that equally divide an inner region of the second closed curve into four parts intersect.

The operation (d) may include calculating an intersection point with the plane only for the 3D triangular surfaces located between the first closed curve and the second closed curve.

The method of recognizing a wound boundary may be implemented in the form of a computer program written to allow a computer to perform each operation of the method of recognizing a wound boundary and recorded in a computer-readable recording medium.

Other specific details of the present disclosure are included in the detailed description and drawings.

Advantageous Effects

According to the present specification, it is possible to improve user convenience by automatically recognizing an accurate wound boundary using artificial intelligence. In addition, it is possible to provide optimal treatment to patients by generating a three-dimensional (3D) wound model based on the accurately recognized wound boundary.

Effects of the present disclosure are not limited to the above-mentioned effects, and other effects that are not mentioned will be clearly understood by those skilled in the art from the following descriptions.

DESCRIPTION OF DRAWINGS

FIG. 1 is an overall flowchart of generating a three-dimensional (3D) wound cover according to the present specification.

FIG. 2 is a more detailed flowchart of a process of producing the 3D wound cover according to the present specification.

FIG. 3 is an artificial intelligence learning method of recognizing a wound boundary according to an embodiment of the present specification.

FIG. 4 is an artificial intelligence learning method of recognizing a wound boundary according to the present specification.

FIG. 5 is a reference diagram of a technique that may be used during learning for recognizing the wound boundary.

FIG. 6 is a reference diagram of post-processing in an artificial intelligence learning method according to the present specification.

FIG. 7 is a flowchart of a method of recognizing a wound boundary according to another embodiment of the present specification.

FIG. 8 is a reference diagram related to the method of recognizing a wound boundary according to the present specification.

FIG. 9 is a reference diagram of a method of recognizing a wound boundary according to another embodiment of the present specification.

FIG. 10 is a reference diagram of a 3D modeled wound after scanning the wound.

FIG. 11 is a method of developing 3D data according to an embodiment of the present specification.

FIG. 12 is a reference diagram for various degrees of a curve equation.

FIG. 13 is a reference diagram for the development of the wound.

FIG. 14 is a diagram for the method of developing 3D data according to the embodiment of the present specification.

FIG. 15 is a method of generating 3D data for a wound cover according to an embodiment of the present specification.

FIG. 16 is an exemplary view of the 3D data for the wound cover.

FIG. 17 is a flowchart of a method of generating 3D data for a wound cover according to another embodiment of the present specification.

MODE FOR INVENTION

Various advantages and features of the present specification and methods accomplishing them will become apparent from the following description of embodiments with reference to the accompanying drawings. However, the present specification is not limited to embodiments to be described below, but may be implemented in various different forms, these embodiments will be provided only in order to make the present specification complete and allow a person with ordinary skill in the art (hereinafter, those skilled in the art) to which the present specification pertains to completely recognize the scope of the present specification, and the scope of the present specification will be defined by the scope of the claims.

Terms used in the present specification are for explaining embodiments rather than limiting the scope of the present specification. Unless otherwise stated, a singular form includes a plural form in the present specification. Throughout this specification, the term "comprise" and/or "comprising" will be understood to imply the inclusion of stated constituents but not the exclusion of any other constituents.

Like reference numerals refer to like components throughout the specification and "and/or" includes each of the components mentioned and includes all combinations thereof. Although "first", "second" and the like are used to describe various components, it goes without saying that these components are not limited by these terms. These terms are used only to distinguish one component from other components. Therefore, it goes without saying that the first component mentioned below may be the second component within the technical scope of the present disclosure.

Unless defined otherwise, all terms (including technical and scientific terms) used in the present specification have the same meaning as meanings commonly understood by those skilled in the art to which the present invention pertains. In addition, terms defined in commonly used dictionary are not ideally or excessively interpreted unless explicitly defined otherwise.

Spatially relative terms "below", "beneath", "lower", "above", "upper", and the like may be used to easily describe the correlation between one component and other components as illustrated in drawings. The spatially relative terms should be understood as terms including different directions of components during use or operation in addition to the directions illustrated in the drawings. For example, if components illustrated in drawings are turned over, components described as "below" or "beneath" of another component may be placed "above" other components. Therefore, the illustrative term "below" can include both downward and upward directions. The components can also be oriented in different directions, and therefore the spatially relative terms can be interpreted according to the orientation. Hereinafter, embodiments of the present disclosure will be described with reference to the accompanying drawings.

FIG. 1 is an overall flowchart of generating a three-dimensional (3D) wound cover according to the present specification.

Referring to FIG. 1, a patient's wound is photographed in a hospital, and the photographed data is transmitted to a 3D wound cover producer through a server. A producer produces a 3D wound cover suitable for the wound by using 3D data of the photographed wound.

FIG. 2 is a more detailed flowchart of a process of producing the 3D wound cover according to the present specification.

Referring to FIG. 2, the wound is first photographed. Since the photographing is for the purpose of generating a 3D model, the wound may be photographed using a device capable of generating 3D data, such as a 3D scanner or an RGB-D camera.

Next, a process of recognizing a wound boundary within the photographed image is required. In the feet of diabetic patients, there are cases where necrosis progresses inward from the skin surface. To produce a 3D wound cover that fills a wound with diabetic foot necrosis, it is necessary to accurately recognize the wound boundary.

Next, the photographed image is converted into 3D data. In this case, the converted 3D data may also include data on the wound boundary already identified.

Next, a 3D model is generated only for the wound. The wound 3D model may be composed of point cloud data represented by three-dimensional coordinates for each point.

Next, it is possible to generate a 3D model for the wound cover by using the wound 3D model. Since the 3D model for the wound cover is a shape that fills the wound, the wound 3D model and the 3D model for the wound cover have a shape corresponding to each other.

Next, a 3D bio-printer outputs the wound cover with a bio-material using the 3D model for the wound cover. The wound cover is attached to a wound to help to fill a necrotic region with new tissue.

Meanwhile, in the present specification, a detailed description of the present disclosure will be made with the diabetic foot necrosis as an example. However, the disclosure described in the present specification is not a technology applied only to the diabetic foot necrosis, and the scope of the present disclosure is not limited by the examples described herein. Hereinafter, each operation will be described in more detail.

Recognition of Wound Boundary

In an image of a photographed wound, the wound and parts other than the wound are photographed together. In this case, in order to accurately distinguish the wound from the parts other than the wound, it is necessary to recognize the wound boundary. As a method of recognizing a wound boundary, there may be a method in which a person directly sets a wound boundary, a method of automatically recognizing a boundary through artificial intelligence learning, and a method of calculating a boundary using 3D data. Among these, the method in which a person directly sets a wound boundary is a method of inputting, by an expert such as a doctor, boundary information using equipment such as a mouse and a touch pen. Therefore, the remaining methods except for the method in which a person directly sets a wound boundary will be described in more detail.

Recognition of Wound Boundary Using Artificial Intelligence Learning

FIG. 3 is an artificial intelligence learning method of recognizing a wound boundary according to an embodiment of the present specification.

Referring to FIG. 3, a schematic flow of the artificial intelligence learning method according to the present specification may be confirmed. Wounds of various patients photographed by a RGB-D camera are prepared as a learning image. An artificial neural network such as deep learning is trained using the learning image, and the learned artificial neural network primarily outputs the results of recognizing a wound boundary. In this case, errors may be included in the wound boundary primarily recognized. This error may be corrected by an expert such as a doctor, and reinforcement learning may be performed by using data recognized as a final boundary again as the learning data.

Such supervised learning or supervised reinforcement learning can improve the performance of the artificial neural network as the amount of learning data increases. However, unlike general object recognition where tens of millions of pieces of image data can be easily obtained, it is very difficult to obtain a large amount of image data (RGB-D image data) as wound image data. For example, in the case of wound image data of diabetic foot necrosis, the status of the wound is very different for each patient, and even the largest public data set contains only about 2,000 to 4,000 images. Therefore, the artificial intelligence learning method according to the present specification suggests a method in which more effective learning can be achieved using a small amount of learning data.

FIG. 4 is an artificial intelligence learning method of recognizing a wound boundary according to the present specification.

Referring to FIG. 4, first, it is possible to store multiple pieces of wound image data in operation S10. The wound image data may be 2D image data or 3D image data.

In the next operation S11, each piece of wound image data may be pre-processed. As an example of the pre-processing, measurement information separation or data augmentation may be included.

The measurement information separation means separating information necessary to determine the size of the wound from the wound image data. When photographing a wound in a hospital, there are many cases where a ruler or a marker is photographed together with the wound to know the size of the wound. Although this information helps to determine the size of the wound in the image data, it does not help much in determining the wound boundary. Therefore, only a region remaining after cutting a region related to a measurement tool in the wound image data may be used as learning image data. In this case, the cut measurement tool region may be separately stored as measurement information (for example, a case where the number of pixels corresponding to 1 cm in a picture is 1,000 is recorded as 0.001) for determining the size of the wound.

The data augmentation refers to a method of increasing limited data to learning data. As the data augmentation, color randomization, adjust image intensity values, enhanced contrast using histogram equalization, contrast-limited adaptive histogram equalization, blurring (Gaussian/Median), affine transformation, brightness randomization, etc. may be used.

In the next operation S12, the artificial neural network can be trained using the learning image data. Since the artificial intelligence learning method according to the present specification is for recognizing the wound boundary, the artificial neural network may be constructed based on a Faster R-CNN network specialized for classification. However, going beyond the level of displaying a bounding box around the wound, RoI Align, Mask R-CNN, Feature Pyramid Network, TTA & Model ensemble techniques may be added/changed and used to accurately recognize the complex wound boundary.

FIG. 5 is a reference diagram of a technique that may be used during learning for recognizing the wound boundary.

Referring to FIG. 5A, the RoI pooling method of the existing Faster R-CNN has a problem that regions of objects recognized by being calculated with integers by discarding decimal places are misaligned on a feature map that is reduced in size through the CNN network. The artificial intelligence learning method according to the present specification may recognize an accurate object region even on the feature map reduced to a decimal unit by using bilinear interpolation for precise segmentation.

Referring to FIG. 5B, the Mask R-CNN structure to which a separate mask network is added may be utilized for a task of segmenting detailed borders of wounds while utilizing Faster R-CNN with good object classification and detection performance. The artificial intelligence learning method according to the present specification performs the classification and maintains Faster R-CNN, which generates the bounding box around an object, as it is, and may configure a separate mask network branch.

Referring to FIG. 5C, it is difficult to predict what size the wound will have in one image, and in some cases, the wound may be close up on the whole picture, and in some cases, the wound may appear very small when photographed from a distance. For this reason, the CNN network structure in which the size of the resulting feature map is smaller than that of the original picture is prone to cause difficulty in recognizing a small wound. Therefore, the artificial intelligence learning method according to the present specification may utilize the feature pyramid network technique of extracting features by up-sampling feature maps in various sizes.

Referring to FIG. 5D, when the prediction is performed on a new wound picture using the previously trained model, different results may be obtained for the same wound depending on an angle, a direction, a size, etc. of a newly photographed picture. In order to prevent this, the artificial intelligence learning method according to the present specification inputs each image to an artificial neural network by variously changing the angle, direction, and size of the image prior to inputting the learning image to the model, thereby performing the prediction. All results may be integrated through Soft NMS to obtain the final prediction result.

Referring to FIG. 5E, various variants are present in Faster R-CNN. The artificial intelligence learning method according to the present specification may perform separate learning using three representative variants (Cascade R-CNN, Deformable Convolution v2, and Prime Sample Attention), and then derive the final prediction result through a weighted boxes fusion technique.

Meanwhile, all of the learning methods described with reference to FIG. 5 are limited to examples, and the artificial intelligence learning method according to the present specification is not limited to the examples.

Referring back to FIG. 4, post-processing may be performed on the results output by the artificial neural network in operation S13. The post-processing may be a task of connecting the boundaries of the wounds recognized by the artificial neural network by a smoother curve.

FIG. 6 is a reference diagram of post-processing in an artificial intelligence learning method according to the present specification.

Referring to FIG. 6, a contour may be recognized from the segmentation recognition result (a). It is possible to extract the minimum number of vertices that may form a contour by using a Douglas-Peucker algorithm (b). All the extracted vertices may be connected by a Catmull-Rom spline algorithm to form a smooth curve without sharp parts (c). In this case, a person may directly move the vertices.

Also, most of the wound photo datasets may contain only an intact wound. However, during actual surgery, an operation of removing damaged or infected tissue called debridement is frequently performed, which causes bleeding. It is easy for such bleeding to produce inaccurate results in predicting the boundary of the wound with a machine learning algorithm, and the following post-processing may be performed to correct these inaccurate results. Bleeding region recognition may measure a bleeding region by assigning different weights to a CIELAB color space and a CMYK color space and combining these weights. ($A(x,y)$: A channel of CIELAB, $M(x,y)$: M channel of CMYK)

Bleeding region=$\alpha*A(x,y)+\beta*M(x,y)$

Edge detection is performed on the bleeding region to extract the boundary, and a point where the wound boundary and the boundary of the bleeding region diverge is found. The gradient for the wound boundary may be calculated, and a coefficient matrix of a polynomial regression curve equation may be obtained according to the gradient around the point. By substituting the curve equation, the wound boundary for the corresponding section may be corrected.

The wound boundary may be recognized in the image of the photographed wound through the artificial neural network trained by the artificial intelligence learning method according to the present specification described above.

Recognition of Border of Wound Using Center Point of Wound

The method of recognizing a wound boundary through artificial intelligence described above may be a method using only RGB data in an image of a wound. However, since the image data of the photographed wound may be RGB-D data, a method of recognizing a wound boundary using depth information of the wound will be described. The method to be described below is a method using characteristics that a gradient of the skin and the wound changes rapidly at the wound boundary.

FIG. 7 is a flowchart of a method of recognizing a wound boundary according to another embodiment of the present specification.

FIG. 8 is a reference diagram related to the method of recognizing a wound boundary according to the present specification.

Referring to FIG. 7, first, it is possible to store the 3D image data of the photographed wound in operation S20. Since the 3D image data has been described above, a repetitive description will be omitted.

In the next operation S21, a point located inside the wound in the image data may be set as a reference point. The reference point is a set of coordinates used for calculations for later determining the wound boundary, and the closer to the center of the wound, the more preferable the reference point.

As an example, in a situation where the wound boundary is not yet known, the coordinates input by the user may be set as the reference point. A user may confirm the 3D image data through the display and rotate the 3D image data so that the border of the wound is most visible. The user may select an arbitrary region within the border of the wound, preferably a central region, by clicking with a mouse.

In the next operation S22, an average normal of a triangle formed by point clouds included in a preset radius around a reference point O may be calculated (refer to FIG. 8A). The 3D image data may be expressed as data about points on three-dimensional coordinates. Points on the three-dimensional coordinates will be referred to as a point cloud, and triangles formed by three points will be referred to as '3D triangular surface' in the present specification. The 3D triangular surface corresponds to a surface of the smallest unit constituting a three-dimensional shape. The preset radius is preferably set large enough to cover both the wound and a normal skin surface beyond the wound boundary. Calculating a normal vector of each 3D triangular surface and calculating an average normal vector using the calculated normal vector are known to those skilled in the art, and thus, a detailed description thereof will be omitted.

The average normal thus calculated may be an axis perpendicular to the entire wound. That is, the average normal may be a central axis that may best represent the entire wound. Accordingly, in the next operation S23, a plane including the average normal and a first axis perpendicular to the normal may be set. Preferably, the 3D image data may be rotated so that the average normal coincides with the Z-axis. In this case, the normal line may be the Z axis, the first axis may be the X axis, and the plane may be the XZ plane (see FIG. 8B).

In the next operation S24, intersection points of the XZ plane and each 3D triangular surface may be calculated, and gradients of each 3D triangular surface may be calculated using the intersection points (see FIG. 8C).

In the next operation S25, it is possible to calculate variations in gradients of adjacent 3D triangular surfaces in a direction away from the reference point.

In the next operation S26, it is possible to select an expected candidate as the wound boundary through two criteria. First, the 3D triangular surfaces related to the variations of gradients maintained at a preset reference gradient change value or less among the calculated variations of gradients are selected. That is, the 3D triangular surfaces whose gradients are not abruptly changed are selected. Then, it is determined whether a length connecting the 3D triangular surfaces connected to each other among the selected 3D triangular surfaces is maintained at a preset reference length value or greater. That is, it is determined whether or not the length is maintained at a certain length or longer without the change in the gradient. When the length is a certain length or longer, a starting point of each length is stored as a candidate list.

The inside of the wound will form a rough surface according to necrosis, and the gradient will change rapidly at the border of the wound. In addition, the region outside the border of the wound, that is, normal skin, will have little change in gradient. Therefore, when a location where a state in which there is little change in gradient is maintained for a certain length or longer is a starting point, the location may be a starting point from the border of the wound to normal skin. Therefore, these starting points are stored as a candidate list.

In the next operation S27, the XZ plane set in the operation S23 may be rotated by a preset angle using the average normal (Z axis) as a rotation axis. In addition, the candidate list may be accumulated while repeating operations S24 to S27 for a new 3D triangular surface that meets the rotating XZ plane.

According to an example, the XZ plane may be rotated clockwise by 0.1°. Therefore, assuming that the starting point is 0°, the candidate list may be accumulated 0 to 3599 times. When the initial starting point of 0° is reached while repeating the above process ('YES' in operation S28), calculations for all 3D triangular surfaces included in the 3D image data may be completed.

In the next operation S29, a closed curve may be formed by connecting adjacent starting points to each other within a preset reference distance (for example, 0.5 mm) among starting points included in the accumulated candidate list. The closed curve may directly correspond to the wound boundary.

When a plurality of closed curves are formed in operation S29, a closed curve including the reference point therein may be selected from among the plurality of closed curves. Also, when there are a plurality of closed curves including the reference point therein, the largest closed curve may be selected.

According to an example of the present specification, a closed curve may be corrected and supplemented by using a location where a surface color (RGB value) in the 3D image data changes to a preset reference color value or greater as additional information. The fact that the colors of the wound and the normal skin are different from each other is used.

Thereafter, the closed curve may be smoothed with a moving average, and the 3D triangular surface information list within the closed curve may be managed as an array (WL). That is, only the 3D shape of the wound may be extracted.

Recognition of Wound Boundary Using Temporary Boundary Line of Wound

Meanwhile, in the method of recognizing a wound boundary described with reference to FIGS. 7 and 8, the calculation is performed on all the 3D triangular surfaces included in the 3D image data. This process may be a factor that lowers the processing speed due to the burden of the amount of computation. When the wound boundary is approximately known, and only the exact boundary may be recognized from the approximate wound boundary, the speed may be improved by reducing the amount of computation.

FIG. 9 is a reference diagram of a method of recognizing a wound boundary according to another embodiment of the present specification.

Referring to FIG. 9A, it may be confirmed that the temporary boundary line is set at the wound boundary. The temporary boundary line may be set through the method of recognizing a wound boundary through the artificial intelligence learning described above with reference to FIG. 4. Also, a user may designate a temporary boundary line of a polygon by clicking the boundary of the wound with a mouse or by touching a screen. In this case, in operation S20 of FIG. 7, it is possible to receive the 3D image data of the photographed wound and temporary boundary line data including the boundary of the wound together.

Referring to FIG. 9B, a first closed curve C1 extending by a preset length based on the temporary boundary line and a second closed curve C2 reduced by a preset length may be generated.

In addition, in operation S21 of FIG. 7, intersection points at which two imaginary lines that equally divide an inner region of the second closed curve into four parts intersect may be set as a reference point. Thereafter, operations S22 and S23 are the same.

On the other hand, in operation S24 of FIG. 7, the intersection point with the plane may be calculated only for the 3D triangular surfaces located between the first closed curve and the second closed curve. That is, the calculation is performed only on the region expected as the wound boundary, not on all the 3D triangular surfaces included in the 3D image data. In this way, the amount of computation may be reduced and the calculation speed can be improved. Thereafter, operations S25 to S29 are the same.

Development of Wound

FIG. 10 is a reference diagram of a 3D modeled wound after scanning the wound.

Referring to FIG. 10, it is possible to confirm the appearance of the 3D modeled wound. As illustrated in FIG. 10, the region of the wound is formed widely from a lower surface to a side surface of a foot, and thus, is curved in a curved shape. When the 3D modeling data is generated for such a wound, the generated 3D model will also take on the curved shape as a whole. When a three-dimensional curved shape is input and output in a bioprinter as it is, the structure may collapse during printing. Therefore, a process of unfolding the curved shape in a horizontal direction so that the bioprinter can output the curved shape is required.

Development of Wound Using Polynomial Regression

FIG. 11 is a method of developing 3D data according to an embodiment of the present specification.

Referring to FIG. 11, first, it is possible to store the 3D image data composed of point clouds for the wound in operation S30. The 3D data composed of the point clouds for the wound may be the 3D data of the wound extracted after executing the method of recognizing a wound boundary described above with reference to FIGS. 7 to 9.

According to the embodiment of the present specification, in operation S30, the 3D data may be rotated on any one of three axes serving as a reference of the three-dimensional coordinates for convenience of subsequent calculations. In this case, the size of the calculated value may be reduced with respect to the point coordinate values of the rotated 3D data. More specifically, the stored 3D data may calculate gradient values for the first axis and the second axis, a vector sum of the calculated gradient values may be calculated, and the stored 3D data may be rotated in a second axis direction by the gradient of the vector sum with respect to the second axis. In this specification, the first axis will be described as "Y axis", the second axis as "X axis", and a third axis as "Z axis." However, the above example is for convenience of understanding, and the present disclosure is not limited to the above example.

In the next operation S31, the 3D data may be divided according to a preset interval based on the Y axis. The 3D data thus divided will be referred to as "slicing 3D data" hereinafter. The smaller the slicing interval, the finer the development, but the amount of computation increases, and the larger the slicing interval, the less the amount of computation, but the development is not fine. For example, the slicing interval may be a 1/n interval (n is a natural number) of an average point interval of a point cloud constituting the 3D data.

In the next operation S32, any one piece of the slicing 3D data may be projected onto the XZ plane. An example in which the slicing 3D data is projected onto the XZ plane may be confirmed at the bottom of FIG. 11.

In the next operation S33, a curve equation of the wound boundary may be calculated through polynomial regression for outer boundary points of the projected slicing 3D data. The curve of the wound boundary may be in the form of a $2^{nd}$ degree function.

FIG. 12 is a reference diagram for various degrees of the curve equation.

Referring to FIG. 12, it can be seen that a $1^{st}$ degree function, a $2^{nd}$ degree function, a $3^{rd}$ degree function, and a $10^{th}$ degree function are shown for the point cloud. It can be seen that the $1^{st}$ degree function is underfitting, and the higher-degree function is overfitting. Considering the characteristics of a wound in the skin tissue of the human body, the $2^{nd}$ degree function may best represent the shape of the wound. The polynomial regression may calculate the curve equation of the wound boundary in the form of the $2^{nd}$ degree function using the following Equation.

$$y = a_0 + a_1 x + a_2 x^2 \qquad \text{(Equation)}$$

-continued $$\begin{bmatrix} n & \sum_{i=1}^{n} x_i & \sum_{i=1}^{n} x_i^2 \\ \sum_{i=1}^{n} x_i & \sum_{i=1}^{n} x_i^2 & \sum_{i=1}^{n} x_i^3 \\ \sum_{i=1}^{n} x_i^2 & \sum_{i=1}^{n} x_i^3 & \sum_{i=1}^{n} x_i^4 \end{bmatrix} \begin{bmatrix} a_0 \\ a_1 \\ a_2 \end{bmatrix} = \begin{bmatrix} \sum_{i=1}^{n} y_i \\ \sum_{i=1}^{n} x_i y_i \\ \sum_{i=1}^{n} x_i^2 y_i \end{bmatrix}$$

Since the polynomial regression is an equation and method known to those skilled in the art, a detailed description thereof will be omitted. However, the curve equation of the wound boundary calculated through the polynomial regression becomes a curve in the form of the $2^{nd}$ degree function that is most closely expresses to the wound boundary of the slicing 3D data.

In the next operation S34, it is possible to calculate the transformed slicing 3D data for the second axis and the third axis by using the following Equation including the curve equation of the wound boundary.

$$x'_i = \sqrt{(x_i - x_{i-1})^2 + (z\_curve_i - z\_curve_{i-1})^2} + x'_{i-1} \qquad \text{[Equation]}$$

$$\_z'_i = z_i - z\_curve_i$$

$z\_curve_i$:equal to $y_i$ of the curve equation of the wound boundary

That is, a difference of transformed 3D slicing data {P'(x', y, z')} from transformed slicing 3D data {P(x, y, z)} is that the wound is developed in the X-axis direction by the distance between the respective points. In this case, Z values of the point cloud constituting the transformed 3D slicing data only have a difference value corresponding to a depth of the wound, and the difference value according to the curved shape of the wound is not reflected.

Meanwhile, operations S32 to S34 are repeatedly executed until applied to all of the slicing 3D data. After all the slicing 3D data is transformed, when the transformed slicing 3D data is integrated again, the shape of the wound developed in the X-axis direction may be obtained.

FIG. 13 is a reference diagram for the development of the wound.

FIG. 13 illustrates a result of developing the wound boundary by point clouds projected onto the XZ plane. As can be seen from the graph, it can be confirmed that the z-axis height decreases and the x-axis length increases as the large curved surface is removed while the small and irregular shape of the wound is maintained. When a shape below is output using a flexible biomaterial in the bioprinter and then attached to the wound, the shape may be modeled to cover the entire wound and cover the fine curves of the wound well.

Development of Wound Using Low-Frequency Filter

FIG. 14 is a diagram for the method of developing 3D data according to the embodiment of the present specification.

Referring to FIG. 14, first, it is possible to store the 3D image data composed of the point clouds for the wound in operation S40. The 3D data composed of the point clouds for the wound may be the 3D data of the wound extracted after executing the method of recognizing a wound boundary described above with reference to FIGS. 7 to 9.

According to the embodiment of the present specification, in operation S40, the 3D data may be rotated on any one of three axes serving as a reference of the three-dimensional coordinates for convenience of subsequent calculations. In this case, the size of the calculated value may be reduced with respect to the point coordinate values of the rotated 3D data. More specifically, the stored 3D data may calculate gradient values for the first axis and the second axis, the vector sum of the calculated gradient values may be calculated, and the stored 3D data may be rotated in a second axis direction by the gradient of the vector sum with respect to the second axis. In this specification, the first axis will be described as "Y axis", the second axis as "X axis", and a third axis as "Z axis". However, the above example is for convenience of understanding, and the present disclosure is not limited to the above example.

In the next operation S41, the 3D data may be divided according to a preset sampling frequency fs based on the Y axis. The 3D data thus divided will be referred to as "slicing 3D data" hereinafter. The higher the sampling frequency fs, the finer the development, but the amount of computation increases, and the lower the sampling frequency fs, the lower the amount of computation, but the development is not fine. For example, the sampling frequency fs may be a 1/n interval (n is a natural number) of the minimum interval of the point cloud. An example of the 3D data sliced by the sampling frequency may be confirmed at the bottom of FIG. 14.

In the next operation S42, a frequency set higher by a preset ratio (a %) than a curved frequency of any one piece of the slicing 3D data among the slicing 3D data may be set as a cutoff frequency fc. For convenience of calculation, the cutoff frequency fc may be expressed below as a differential equation after subjected to inverse Laplace transform.

$$y_n = \frac{\tau}{\tau + t_s} y_{n-1} + \frac{t_s}{\tau + t_s} x_n \quad \text{[Equation]}$$

$$\tau = \frac{1}{2\pi f_c}$$

In the next operation S43, a curve point may be calculated by passing the slicing 3D data through a low-frequency filter having the cut-off frequency fc. In operation S43, padding data may be further added back and forth at a point where the value for the Y axis is 0 among the slicing 3D data, and the resultant may pass through the low frequency filter. The curve point $P_{curve_{y=0}}(x, y_0, z\_curve)$ thus calculated may be expressed as follows.

$$z\_curve_n = \frac{\tau}{\tau + t_s} z\_curv_{en-1} + \frac{t_s}{\tau + t_s} x_n \quad \text{[Equation]}$$

In the next operation S44, the transformed slicing 3D data for the X and Y axes is calculated using the following Equation including the curve points.

It is possible to calculate the transformed slicing 3D data for the second axis and the third axis by using the following Equation including the curve equation of the wound boundary.

$$x'_i = \sqrt{(x_i - x_{i-1})^2 + (z\_curve_i - z\_curve_{i-1})^2} + x'_{i-1} \quad \text{[Equation]}$$

$$z'_i = z_i - z\_curve_i$$

z_curve$_i$:equal to $y_i$ of curve point

That is, a difference of transformed 3D slicing data {P'(x', y, z')} from transformed slicing 3D data {P'(x, y, z_curve$_i$)} is that the wound is developed in the X-axis direction by the distance between the respective points. In this case, Z values of the point cloud constituting the transformed 3D slicing data only have a difference value corresponding to a depth of the wound, and the difference value according to the curved shape of the wound is not reflected.

Meanwhile, operations S42 to S44 are repeatedly executed until applied to all of the slicing 3D data. After all the slicing 3D data is transformed, when the transformed slicing 3D data is integrated again, the shape of the wound developed in the X-axis direction may be obtained. The above contents have been described with reference to FIG. 13, and therefore, a repetitive description thereof will be omitted.

Wound Cover

According to the method of developing 3D data described with reference to FIG. 11 or FIG. 14, it is possible to secure 3D data that the bioprinter can output. However, the 3D data obtained in this process is data for the wound, and what is required in the present disclosure is data for the cover that may cover the wound.

Method of Generating 3D Data for Wound Cover

FIG. 15 is a method of generating 3D data for a wound cover according to an embodiment of the present specification.

Referring to FIG. 15, first, it is possible to store the 3D image data composed of the point clouds for the developed wound in operation S50. The 3D data of the developed wound may be obtained according to the method of developing 3D data described with reference to FIG. 11 or FIG. 14.

According to the embodiment of the present specification, in operation S50, the 3D data may be rotated on any one of three axes serving as a reference of the three-dimensional coordinates for convenience of subsequent calculations. In this case, the size of the calculated value may be reduced with respect to the point coordinate values of the rotated 3D data. More specifically, the stored 3D data may calculate gradient values for the first axis and the second axis, the vector sum of the calculated gradient values may be calculated, and the stored 3D data may be rotated in a second axis direction by the gradient of the vector sum with respect to the second axis. In this specification, the first axis will be described as "Y axis", the second axis as "X axis", and a third axis as "Z axis". However, the above example is for convenience of understanding, and the present disclosure is not limited to the above example.

In the next operation S51, among the point clouds constituting the 3D data, the point cloud located inside may be removed based on the wound boundary. In this case, the boundary may mean the edge of the wound shape, that is, the outermost point forming the wound as well as the boundary with normal skin.

In the next operation S52, the 3D data may be divided according to a preset interval based on the Y axis. For example, the sampling frequency fs may be a 1/n interval (n is a natural number) of the minimum interval of the point cloud. An example of the 3D data sliced by the sampling frequency may be confirmed at the bottom of FIG. 15.

In the next operation S53, the curve equation may be calculated through the polynomial regression for the slicing 3D data. The process of obtaining the curve equation through the polynomial regression has been described in the method of developing a wound described above with reference to FIG. 11, and is a process known to those skilled in the art, and a repetitive description thereof will be omitted.

In the next operation S54, (X, Y) coordinate values of the point cloud included in the slicing 3D data may be substituted into the curve equation to calculate (Z) coordinate values. The coordinate values (X, Y, Z) thus calculated correspond to "cover point clouds".

In the next operation S55, it is possible to remove a point outside the wound boundary among the cover point clouds and combine the point with the point cloud for the developed wound.

FIG. 16 is an exemplary view of the 3D data for the wound cover.

Referring to FIG. 16, a cover having a shape that may cover the wound may be confirmed. It can be seen that the upper portion of the cover has a flat shape similar to the skin surface, and the lower portion has an irregular shape corresponding to the shape of the wound.

Method of Generating 3D Data for Wound Cover Considering Wound Cover Output

Meanwhile, the wound cover illustrated in FIG. 16 is formed to reflect the presence of normal skin on the edge of the wound. Therefore, as can be seen in FIG. 16, the outermost boundary surface of the wound cover may have a vertically cut shape. When the vertically cut shape is output by the bioprinter as it is, the outer area of the cover may collapse.

FIG. 17 is a flowchart of a method of generating 3D data for a wound cover according to another embodiment of the present specification.

Referring to FIG. 17, the method of generating 3D data for a wound cover according to another embodiment of the present specification may be performed after the last process S55 of FIG. 15 above.

First, in operation S56, it is possible to calculate the boundary points having the maximum value with respect to the Z axis among the point clouds constituting the 3D data of the developed wound.

In the next operation S57, all values for the Z-axis of the boundary points may be substituted with the maximum value.

In the next operation S58, the Z value of the point cloud may be filled with the maximum value up to a point extending by a preset offset in the X and Y directions of the boundary points. In addition, the Z value of the point cloud may be filled with 0 from the point after the offset. That is, in the process of manufacturing the wound cover, it is a process of erecting a wall of a container that may contain the wound cover. Referring to the lower part of FIG. 17, the 3D shape of the container for manufacturing the wound cover generated through the above process may be confirmed.

The method may be implemented with processors, application-specific integrated circuits (ASICs), other chipsets, logic circuits, registers, communication modems, data processing devices, etc. known in the art for executing calculations and various control logics to which the present disclosure pertains. In addition, when the above-described control logic is implemented in software, the control unit may be implemented as a set of program modules. In this case, the program module may be stored in the memory device and executed by the processor.

In order for the computer to read the program and execute the methods implemented as a program, the program may include code coded in a computer language such as C/C++, C#, JAVA, Python, machine language, and the like that the processor (CPU) of the computer can read through a device interface of the computer. Such code may include functional code related to functions defining functions necessary for executing the methods, or the like, and include an execution procedure related to control code necessary for the processor of the computer to execute the functions according to a predetermined procedure. In addition, such code may further include memory reference related code for which a location (address, house number) of the internal or external memory of the computer additional information or media necessary for the processor of the computer to execute the functions should be referenced. In addition, when the processor of the computer needs to communicate with any other computers, servers, or the like located remotely in order to execute the above functions, the code may further include communication-related code for how to communicate with any other computers, servers, or the like located remotely using a communication module of the computer, how to transmit/receive any information or media during communication, or the like The storage medium is not a medium that stores data therein for a while, such as a register, a cache, a memory, or the like, but means a medium that semi-permanently stores data therein and is readable by a device. Specifically, examples of the storage medium include, but are not limited to, a ROM, a RAM, a CD-ROM, a magnetic tape, a floppy disk, an optical data storage device, and the like. That is, the program may be stored in various recording media on various servers accessible by the computer or in various recording media on the computer of the user. In addition, the medium may be distributed in a computer system connected by a network, and store computer-readable code in a distributed manner.

Although exemplary embodiments of the present invention has been described with reference to the accompanying drawings, those skilled in the art to which the present specification belongs will appreciate that various modifications and alterations may be made without departing from the spirit or essential feature of the present specification. Therefore, it is to be understood that the exemplary embodiments described hereinabove are illustrative rather than being restrictive in all aspects.

The invention claimed is:

1. A method of recognizing a wound boundary using three-dimensional (3D) image data of the photographed wound, the method comprising:
   (a) storing, by processor, the 3D image data of the photographed wound;
   (b) setting, by processor, a point located inside the wound in the image data as a reference point;
   (c) calculating, by processor, an average normal of triangles (hereinafter, "3D triangular surfaces") formed by point clouds included in a preset radius around the reference point, and setting, by processor, a plane including the average normal and a first axis perpendicular to the normal;

(d) calculating, by processor, intersection points between the plane and each of the 3D triangular surfaces, and calculating, by processor, gradients of each of the 3D triangular surfaces using the intersection point;

(e) calculating, by processor, variations of gradients of adjacent 3D triangular surfaces in a direction away from the reference point;

(f) storing, by processor, as a candidate list, a starting point having a length that is maintained at greater than or equal to a reference length value in which a length connecting the 3D triangular surfaces connected to each other among the 3D triangular surfaces related to the variations of the gradients is maintained at a preset reference gradient change value or less among the calculated variations of the gradients;

(g) accumulating, by processor, the candidate list stored in the operation (f) while rotating the plane set in the operation (c) at a preset angle using the average normal as a rotation axis and repeating the operations (d) to (f); and (h) forming, by processor, a closed curve by connecting adjacent starting points within a preset reference distance among the starting points included in the accumulated candidate list.

2. The method of claim 1, wherein the operation (b) includes setting coordinates input by a user as the reference point.

3. The method of claim 1, wherein the normal is a Z axis, the first axis is an X axis, and the plane is an XZ plane.

4. The method of claim 1, wherein the operation (g) includes rotating the plane clockwise by 0.1°.

5. The method of claim 1, wherein the operation (h) includes, when a plurality of closed curves are formed, selecting a closed curve including the reference point therein from among the plurality of closed curves.

6. The method of claim 5, wherein the operation (h) further includes, when there are the plurality of closed curves including the reference point therein, selecting a largest closed curve.

7. The method of claim 1, wherein the operation (a) includes:

(a-1) receiving, by processor, temporary boundary line data including the 3Dd image data of the photographed wound and a boundary of the wound; and (a-2) generating, by processor, a first closed curve extending by a preset length based on the temporary boundary line and a second closed curve reduced by the preset length.

8. The method of claim 7, wherein the operation (b) includes setting, as the reference point, an intersection point where two imaginary lines that equally divide an inner region of the second closed curve into four parts intersect.

9. The method of claim 7, wherein the operation (d) includes calculating an intersection point with the plane only for the 3D triangular surfaces located between the first closed curve and the second closed curve.

10. A computer program written to allow a computer to perform each operation of the method of recognizing a wound boundary according to claim 1 and recorded in a computer-readable recording medium.

* * * * *